United States Patent
Kleckner et al.

(10) Patent No.: US 7,941,214 B2
(45) Date of Patent: May 10, 2011

(54) METHOD AND APPARATUS FOR DETECTING ARRHYTHMIAS IN A SUBCUTANEOUS MEDICAL DEVICE

(75) Inventors: Karen J. Kleckner, New Brighton, MN (US); Robert W. Stadler, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 980 days.

(21) Appl. No.: 11/557,597

(22) Filed: Nov. 8, 2006

(65) Prior Publication Data

US 2007/0232945 A1    Oct. 4, 2007

(51) Int. Cl.
*A61N 1/39* (2006.01)
(52) U.S. Cl. ............................ 607/5; 607/4
(58) Field of Classification Search ............ 607/5, 4
See application file for complete search history.

(56) References Cited

U.S. PATENT DOCUMENTS

| | | |
|---|---|---|
| 4,180,078 A | 12/1979 | Anderson |
| 4,374,382 A | 2/1983 | Markowitz |
| 4,548,209 A | 10/1985 | Wielders et al. |
| 4,556,063 A | 12/1985 | Thompson et al. |
| 4,567,892 A | 2/1986 | Plicchi et al. |
| 5,117,824 A | 6/1992 | Keimel et al. |
| 5,127,404 A | 7/1992 | Wyborny et al. |
| 5,163,427 A | 11/1992 | Keimel |
| 5,176,137 A | 1/1993 | Erickson et al. |
| 5,188,105 A | 2/1993 | Keimel |
| 5,191,884 A * | 3/1993 | Gilli et al. ................. 607/5 |
| 5,193,535 A | 3/1993 | Bardy et al. |
| 5,331,966 A | 7/1994 | Bennett et al. |
| 5,354,316 A | 10/1994 | Keimel |
| 5,464,434 A | 11/1995 | Alt |
| 5,470,345 A | 11/1995 | Hassler et al. |
| 5,545,186 A | 8/1996 | Olson et al. |
| 5,593,431 A | 1/1997 | Sheldon |
| 5,683,432 A | 11/1997 | Goedeke et al. |
| 5,855,593 A | 1/1999 | Olson et al. |
| 6,134,479 A * | 10/2000 | Brewer et al. ............... 607/142 |
| 6,236,882 B1 | 5/2001 | Lee et al. |
| 6,304,773 B1 | 10/2001 | Taylor et al. |
| 6,505,067 B1 | 1/2003 | Lee et al. |
| 6,512,940 B1 | 1/2003 | Brabec et al. |
| 6,522,915 B1 | 2/2003 | Ceballos et al. |
| 6,622,046 B2 | 9/2003 | Fraley et al. |
| 6,754,528 B2 * | 6/2004 | Bardy et al. ................. 607/5 |

(Continued)

FOREIGN PATENT DOCUMENTS

WO   WO 0241946   5/2002

(Continued)

OTHER PUBLICATIONS

International Search Report, PCT/US2007/063784, Apr. 9, 2007, 5 pages.

*Primary Examiner* — Carl H Layno
*Assistant Examiner* — Luther G Behringer
(74) *Attorney, Agent, or Firm* — Michael C. Soldner

(57) ABSTRACT

A method and apparatus for detecting a cardiac event in a medical device that includes sensing cardiac signals from a plurality of electrodes, charging an energy storage device in response to the sensed cardiac signals, determining whether the charging of the energy storage device is completed, and determining whether the cardiac event is confirmed in response to an asynchronous look back.

17 Claims, 20 Drawing Sheets

U.S. PATENT DOCUMENTS

| | | |
|---|---|---|
| 6,873,870 B2 | 3/2005 | Ferek-Petric |
| 6,879,856 B2 | 4/2005 | Stadler et al. |
| 6,892,094 B2 * | 5/2005 | Ousdigian et al. ............. 607/4 |
| 2003/0083587 A1 | 5/2003 | Ferek-Petric |
| 2003/0097153 A1 | 5/2003 | Bardy et al. |
| 2003/0120312 A1 * | 6/2003 | Cammilli et al. ............. 607/5 |
| 2004/0111121 A1 | 6/2004 | Brown et al. |
| 2004/0172071 A1 | 9/2004 | Bardy et al. |
| 2004/0220629 A1 | 11/2004 | Kamath et al. |
| 2004/0236379 A1 | 11/2004 | Bardy et al. |
| 2004/0254613 A1 | 12/2004 | Ostroff et al. |
| 2004/0260350 A1 | 12/2004 | Brandstetter et al. |
| 2005/0010251 A9 | 1/2005 | Bardy et al. |
| 2005/0049644 A1 | 3/2005 | Warren et al. |
| 2005/0119707 A1 | 6/2005 | Hauser et al. |
| 2005/0119708 A1 | 6/2005 | Haefner |
| 2005/0131464 A1 | 6/2005 | Heinrich et al. |
| 2005/0143776 A1 | 6/2005 | Brown |
| 2006/0142809 A1 * | 6/2006 | Kroll et al. ............. 607/5 |

FOREIGN PATENT DOCUMENTS

| | | |
|---|---|---|
| WO | WO 2004023995 | 3/2004 |
| WO | WO 2004105871 | 12/2004 |
| WO | WO 2005011809 | 2/2005 |
| WO | WO 2006020198 | 2/2006 |

* cited by examiner

METHOD AND APPARATUS FOR DETECTING ARRHYTHMIAS IN A SUBCUTANEOUS MEDICAL DEVICE

FIELD OF THE INVENTION

The present invention generally relates to an implantable medical device system, and more particularly to a method and apparatus for detecting arrhythmias in a subcutaneous medical device.

BACKGROUND OF THE INVENTION

Many types of implantable medical devices (IMDs) have been implanted that deliver relatively high-energy cardioversion and/or defibrillation shocks to a patient's heart when a malignant tachyarrhythmia, e.g., ventricular tachycardia or ventricular fibrillation, is detected. Cardioversion shocks are typically delivered in synchrony with a detected R-wave when fibrillation detection criteria are met, whereas defibrillation shocks are typically delivered when fibrillation criteria are met and an R-wave cannot be discerned from the electrogram (EGM).

The current state of the art of ICDs or implantable pacemaker/cardioverter/defibrillators (PCDs) includes a full featured set of extensive programmable parameters which includes multiple arrhythmia detection criteria, multiple therapy prescriptions (for example, stimulation for pacing in the atrial, ventricular and/or both chambers, bi-atrial and/or bi-ventricular pacing, arrhythmia overdrive or entrainment stimulation, and high level stimulation for cardioversion and/ or defibrillation), extensive diagnostic capabilities and high speed telemetry systems.

Current technology for the implantation of an IMD uses a transvenous approach for cardiac electrodes and lead wires. The defibrillator canister/housing is generally implanted as an active can for defibrillation and electrodes positioned in the heart are used for pacing, sensing and detection of arrhythmias.

Attempts are being made to identify patients who are asymptomatic by conventional measures but are nevertheless at risk of a future sudden death episode. Current studies of patient populations, e.g., the MADIT II and SCDHeFT studies, are establishing that there are large numbers of patients in any given population that are susceptible to sudden cardiac death, that they can be identified with some degree of certainty and that they are candidates for a prophylactic implantation of a defibrillator (often called primary prevention).

One option proposed for this patient population is to implant a prophylactic subcutaneous implantable device (SubQ device). As SubQ device technology evolves, it may develop a clear and distinct advantage over non-SubQ devices. For example, the SubQ device does not require leads to be placed in the bloodstream. Accordingly, complications arising from leads placed in the cardiovasculature environment are eliminated. Further, endocardial lead placement is not possible with patients who have a mechanical heart valve implant and is not generally recommended for pediatric cardiac patients. For these and other reasons, a SubQ device may be preferred over an ICD.

There are technical challenges associated with the operation of a SubQ device. For example, SubQ device sensing is challenged by the presence of muscle artifact, respiration and other physiological signal sources. This is particularly because the SubQ device is limited to far-field sensing since there are no intracardial or epicardial electrodes in a subcutaneous system. Further, sensing of atrial activation from subcutaneous electrodes is limited since the atria represent a small muscle mass and the atrial signals are not sufficiently detectable transthoracically.

Yet another challenge could occur in situations where it is desirable to combine a SubQ device with an existing pacemaker (IPG) in a patient. While this may be desirable in a case where an IPG patient may need a defibrillator, a combination implant of a SubQ device and an IPG may result in inappropriate therapy by the SubQ device, which may pace or shock based on spikes from the IPG. Specifically, each time the IPG emits a pacing stimulus, the SubQ device may interpret it as a genuine cardiac beat. The result can be over-counting beats from the atrium, ventricles or both; or, because of the larger pacing spikes, sensing of arrhythmic signals (which are typically much smaller in amplitude) may be compromised.

Therefore, for these and other reasons, a need exists for an improved method and apparatus to reliably sense and detect arrhythmias in a subcutaneous device, while rejecting noise and other physiologic signals.

BRIEF DESCRIPTION OF THE DRAWINGS

Aspects and features of the present invention will be appreciated as the same becomes better understood by reference to the following detailed description of the embodiments of the invention when considered in connection with the accompanying drawings, wherein.

DETAILED DESCRIPTION OF THE INVENTION

Figure 1:
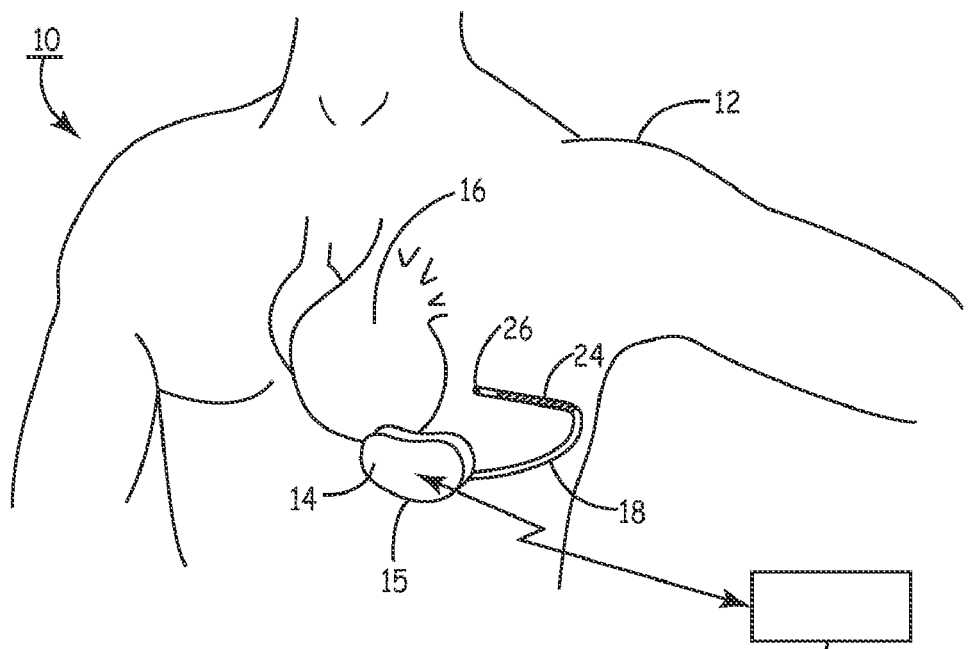
FIG. 1 is a schematic diagram of an exemplary subcutaneous device in which the present invention may be usefully practiced.

FIG. 1 is a schematic diagram of an exemplary subcutaneous device in which the present invention may be usefully practiced. As illustrated in FIG. 1, a subcutaneous device 14 according to an embodiment of the present invention is subcutaneously implanted outside the ribcage of a patient 12, anterior to the cardiac notch. Further, a subcutaneous sensing and cardioversion/defibrillation therapy delivery lead 18 in electrical communication with subcutaneous device 14 is tunneled subcutaneously into a location adjacent to a portion of a latissimus dorsi muscle of patient 12. Specifically, lead 18 is tunneled subcutaneously from the median implant pocket of the subcutaneous device 14 laterally and posterially to the patient's back to a location opposite the heart such that the heart 16 is disposed between the subcutaneous device 14 and the distal electrode coil 24 and distal sensing electrode 26 of lead 18.

It is understood that while the subcutaneous device 14 is shown positioned through loose connective tissue between the skin and muscle layer of the patient, the term "subcutaneous device" is intended to include a device that can be positioned in the patient to be implanted using any non-intravenous location of the patient, such as below the muscle layer or within the thoracic cavity, for example.

Further referring to FIG. 1, a programmer 20 is shown in telemetric communication with subcutaneous device 14 by an RF communication link 22. Communication link 22 may be any appropriate RF link such as Bluetooth, WiFi, MICS, or as described in U.S. Pat. No. 5,683,432 "Adaptive Performance-Optimizing Communication System for Communicating with an Implantable Medical Device" to Goedeke, et al and incorporated herein by reference in its entirety.

Subcutaneous device 14 includes a housing 15 that may be constructed of stainless steel, titanium or ceramic as described in U.S. Pat. No. 4,180,078 "Lead Connector for a Body Implantable Stimulator" to Anderson and U.S. Pat. No. 5,470,345 "Implantable Medical Device with Multi-layered Ceramic Enclosure" to Hassler, et al, both incorporated herein by reference in their entireties. The electronics circuitry of SubQ ICD 14 may be incorporated on a polyimide flex circuit, printed circuit board (PCB) or ceramic substrate with integrated circuits packaged in leadless chip carriers and/or chip scale packaging (CSP).

Subcutaneous lead 18 includes a distal defibrillation coil electrode 24, a distal sensing electrode 26, an insulated flexible lead body and a proximal connector pin 27 (shown in FIG. 2) for connection to the housing 15 of the subcutaneous device 14 via a connector 25. In addition, one or more electrodes 28 (shown in FIG. 2) are positioned along the outer surface of the housing to form a housing-based subcutaneous electrode array (SEA). Distal sensing electrode 26 is sized appropriately to match the sensing impedance of the housing-based subcutaneous electrode array.

It is understood that while device 14 is shown with electrodes 28 positioned on housing 15, according to an embodiment of the present invention electrodes 28 may be alternatively positioned along one or more separate leads connected to device 14 via connector 25.

Figure 2:
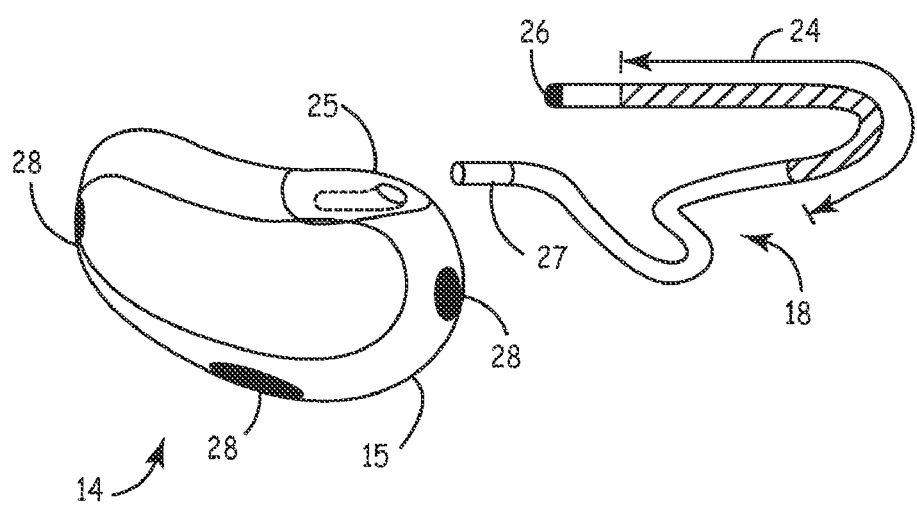
FIG. 2 is a schematic diagram of the implantable medical device of FIG. 1, according to one exemplary embodiment of the invention.

Continuing with FIG. 2, electrodes 28 are welded into place on the flattened periphery of the housing 15. In the embodiment depicted in this figure, the complete periphery of the SubQ ICD may be manufactured to have a slightly flattened perspective with rounded edges to accommodate the placement of the electrodes 28. The electrodes 28 are welded to housing 15 (to preserve hermaticity) and are connected via wires (not shown) to electronic circuitry (described herein below) inside housing 15. Electrodes 28 may be constructed of flat plates, or alternatively, may be spiral electrodes as described in U.S. Pat. No. 6,512,940 "Subcutaneous Spiral Electrode for Sensing Electrical Signals of the Heart" to Brabec, et al and mounted in a non-conductive surround shroud as described in U.S. Pat. No. 6,522,915 "Surround Shroud Connector and Electrode Housings for a Subcutaneous Electrode Array and Leadless ECGs" to Ceballos, et al and U.S. Pat. No. 6,622,046 "Subcutaneous Sensing Feedthrough/Electrode Assembly" to Fraley, et al, all incorporated herein by reference in their entireties. The electrodes 28 of FIG. 2 can be positioned to form orthogonal or equilateral signal vectors, for example.

The electronic circuitry employed in subcutaneous device 14 can take any of the known forms that detect a tachyarrhythmia from the sensed ECG and provide cardioversion/defibrillation shocks as well as post-shock pacing as needed while the heart recovers. A simplified block diagram of such circuitry adapted to function employing the first and second cardioversion-defibrillation electrodes as well as the ECG sensing and pacing electrodes described herein below is set forth in FIG. 3. It will be understood that the simplified block diagram does not show all of the conventional components and circuitry of such devices including digital clocks and clock lines, low voltage power supply and supply lines for powering the circuits and providing pacing pulses or telemetry circuits for telemetry transmissions between the device 14 and external programmer 20.

Figure 3:
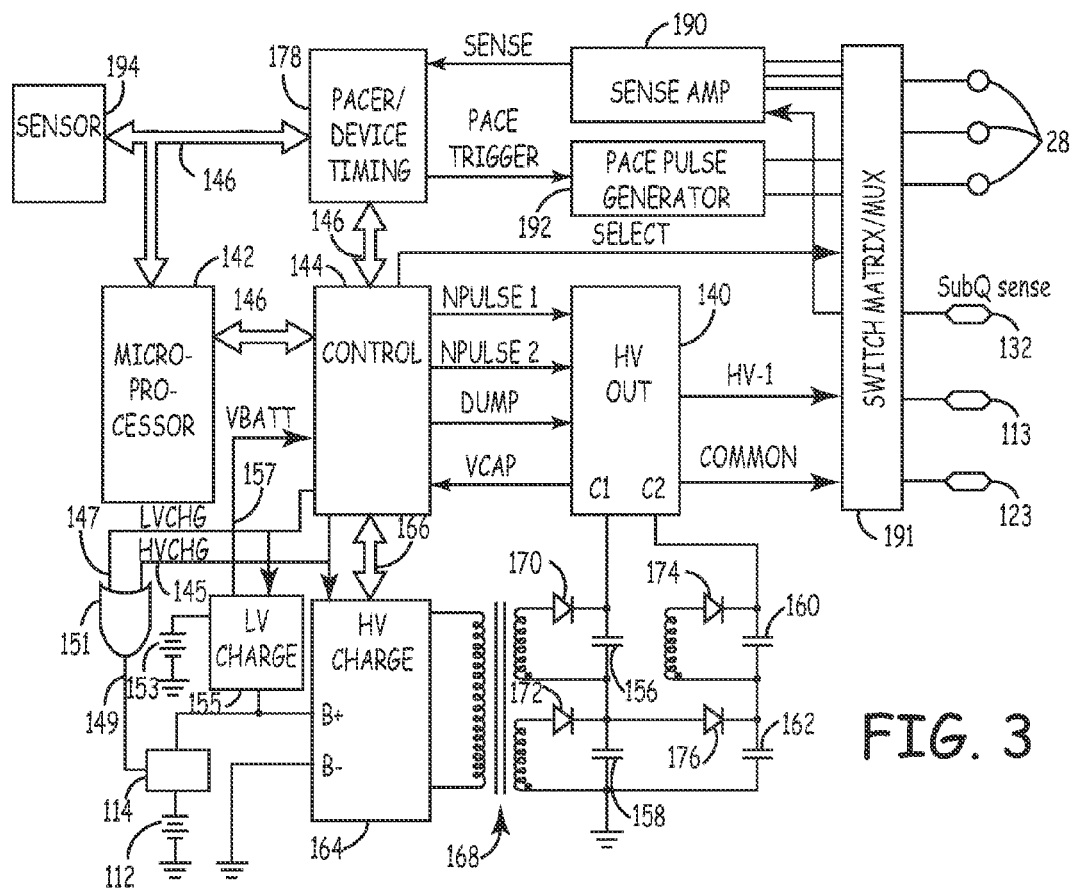
FIG. 3 is an exemplary schematic diagram of electronic circuitry within a hermetically sealed housing of a subcutaneous device of the present invention.

FIG. 3 is an exemplary schematic diagram of electronic circuitry within a hermetically sealed housing of a subcutaneous device according to an embodiment of the present invention. As illustrated in FIG. 3, subcutaneous device 14 includes a low voltage battery 153 coupled to a power supply (not shown) that supplies power to the circuitry of the subcutaneous device 14 and the pacing output capacitors to supply pacing energy in a manner well known in the art. The low voltage battery 153 may be formed of one or two conventional $LiCF_x$, $LiMnO_2$ or $LiI_2$ cells, for example. The subcutaneous device 14 also includes a high voltage battery 112 that may be formed of one or two conventional LiSVO or $LiMnO_2$ cells. Although two both low voltage battery and a high voltage battery are shown in FIG. 3, according to an embodiment of the present invention, the device 14 could utilize a single battery for both high and low voltage uses.

Further referring to FIG. 3, subcutaneous device 14 functions are controlled by means of software, firmware and hardware that cooperatively monitor the ECG, determine when a cardioversion-defibrillation shock or pacing is necessary, and deliver prescribed cardioversion-defibrillation and pacing therapies. The subcutaneous device 14 may incorporate circuitry set forth in commonly assigned U.S. Pat. No. 5,163,427 "Apparatus for Delivering Single and Multiple Cardioversion and Defibrillation Pulses" to Keimel and U.S. Pat. No. 5,188,105 "Apparatus and Method for Treating a Tachyarrhythmia" to Keimel for selectively delivering single phase, simultaneous biphasic and sequential biphasic cardioversion-defibrillation shocks typically employing ICD IPG housing electrodes 28 coupled to the COMMON output 123 of high voltage output circuit 140 and cardioversion-defibrillation electrode 24 disposed posteriorly and subcutaneously and coupled to the HVI output 113 of the high voltage output circuit 140. Outputs 132 of FIG. 3 is coupled to sense electrode 26.

The cardioversion-defibrillation shock energy and capacitor charge voltages can be intermediate to those supplied by ICDs having at least one cardioversion-defibrillation electrode in contact with the heart and most AEDs having cardioversion-defibrillation electrodes in contact with the skin. The typical maximum voltage necessary for ICDs using most biphasic waveforms is approximately 750 Volts with an associated maximum energy of approximately 40 Joules. The typical maximum voltage necessary for AEDs is approximately 2000-5000 Volts with an associated maximum energy of approximately 200-360 Joules depending upon the model and waveform used. The subcutaneous device 14 of the present invention uses maximum voltages in the range of about 300 to approximately 1000 Volts and is associated with energies of approximately 25 to 150 joules or more. The total high voltage capacitance could range from about 50 to about 300 microfarads. Such cardioversion-defibrillation shocks are only delivered when a malignant tachyarrhythmia, e.g., ventricular fibrillation is detected through processing of the far field cardiac ECG employing the detection algorithms as described herein below.

In FIG. 3, sense amp 190 in conjunction with pacer/device timing circuit 178 processes the far field ECG sense signal that is developed across a particular ECG sense vector defined by a selected pair of the subcutaneous electrodes 24, 26 and 28, or, optionally, a virtual signal (i.e., a mathematical combination of two vectors) if selected. The selection of the sensing electrode pair is made through the switch matrix/MUX 191 in a manner to provide the most reliable sensing of the ECG signal of interest, which would be the R wave for patients who are believed to be at risk of ventricular fibrillation leading to sudden death. The far field ECG signals are passed through the switch matrix/MUX 191 to the input of the sense amplifier 190 that, in conjunction with pacer/device timing circuit 178, evaluates the sensed EGM. Bradycardia, or asystole, is typically determined by an escape interval timer within the pacer timing circuit 178 and/or the control circuit 144. Pace Trigger signals are applied to the pacing pulse generator 192 generating pacing stimulation when the interval between successive R-waves exceeds the escape interval. Bradycardia pacing is often temporarily provided to maintain cardiac output after delivery of a cardioversion-defibrillation shock that may cause the heart to slowly beat as it recovers back to normal function. Sensing subcutaneous far field signals in the presence of noise may be aided by the use of appropriate denial and extensible accommodation periods as described in U.S. Pat. No. 6,236,882 "Noise Rejection for Monitoring ECGs" to Lee, et al and incorporated herein by reference in its' entirety.

Detection of a malignant tachyarrhythmia is determined in the Control circuit 144 as a function of the intervals between R-wave sense event signals that are output from the pacer/device timing 178 and sense amplifier circuit 190 to the timing and control circuit 144. It should be noted that the present invention utilizes not only interval based signal analysis method but also supplemental sensors and morphology processing method and apparatus as described herein below.

Supplemental sensors such as tissue color, tissue oxygenation, respiration, patient activity and the like may be used to contribute to the decision to apply or withhold a defibrillation therapy as described generally in U.S. Pat. No. 5,464,434 "Medical Interventional Device Responsive to Sudden Hemodynamic Change" to Alt and incorporated herein by reference in its entirety. Sensor processing block 194 provides sensor data to microprocessor 142 via data bus 146. Specifically, patient activity and/or posture may be determined by the apparatus and method as described in U.S. Pat. No. 5,593,431 "Medical Service Employing Multiple DC Accelerometers for Patient Activity and Posture Sensing and Method" to Sheldon and incorporated herein by reference in its entirety. Patient respiration may be determined by the apparatus and method as described in U.S. Pat. No. 4,567,892 "Implantable Cardiac Pacemaker" to Plicchi, et al and incorporated herein by reference in its entirety. Patient tissue oxygenation or tissue color may be determined by the sensor apparatus and method as described in U.S. Pat. No. 5,176,137 to Erickson, et al and incorporated herein by reference in its entirety. The oxygen sensor of the '137 patent may be located in the subcutaneous device pocket or, alternatively, located on the lead 18 to enable the sensing of contacting or near-contacting tissue oxygenation or color.

Certain steps in the performance of the detection algorithm criteria are cooperatively performed in microcomputer 142, including microprocessor, RAM and ROM, associated circuitry, and stored detection criteria that may be programmed into RAM via a telemetry interface (not shown) conventional in the art. Data and commands are exchanged between microcomputer 142 and timing and control circuit 144, pacer timing/amplifier circuit 178, and high voltage output circuit 140 via a bi-directional data/control bus 146. The pacer timing/amplifier circuit 178 and the control circuit 144 are clocked at a slow clock rate. The microcomputer 142 is normally asleep, but is awakened and operated by a fast clock by interrupts developed by each R-wave sense event, on receipt of a downlink telemetry programming instruction or upon delivery of cardiac pacing pulses to perform any necessary mathematical calculations, to perform tachycardia and fibrillation detection procedures, and to update the time intervals monitored and controlled by the timers in pacer/device timing circuitry 178.

When a malignant tachycardia is detected, high voltage capacitors 156, 158, 160, and 162 are charged to a pre-programmed voltage level by a high-voltage charging circuit 164. It is generally considered inefficient to maintain a constant charge on the high voltage output capacitors 156, 158, 160, 162. Instead, charging is initiated when control circuit 144 issues a high voltage charge command HVCHG delivered on line 145 to high voltage charge circuit 164 and charging is controlled by means of bi-directional control/data bus 166 and a feedback signal VCAP from the HV output circuit 140. High voltage output capacitors 156, 158, 160 and 162 may be of film, aluminum electrolytic or wet tantalum construction.

The negative terminal of high voltage battery 112 is directly coupled to system ground. Switch circuit 114 is normally open so that the positive terminal of high voltage battery 112 is disconnected from the positive power input of the high voltage charge circuit 164. The high voltage charge command HVCHG is also conducted via conductor 149 to the control input of switch circuit 114, and switch circuit 114 closes in response to connect positive high voltage battery voltage EXT B+ to the positive power input of high voltage charge circuit 164. Switch circuit 114 may be, for example, a field effect transistor (FET) with its source-to-drain path interrupting the EXT B+ conductor 118 and its gate receiving the HVCHG signal on conductor 145. High voltage charge circuit 164 is thereby rendered ready to begin charging the high voltage output capacitors 156, 158, 160, and 162 with charging current from high voltage battery 112.

High voltage output capacitors 156, 158, 160, and 162 may be charged to very high voltages, e.g., 300-1000V, to be discharged through the body and heart between the electrode pair of subcutaneous cardioversion-defibrillation electrodes 113 and 123. The details of the voltage charging circuitry are also not deemed to be critical with regard to practicing the present invention; one high voltage charging circuit believed to be suitable for the purposes of the present invention is disclosed. High voltage capacitors 156, 158, 160 and 162 may be charged, for example, by high voltage charge circuit 164 and a high frequency, high-voltage transformer 168 as described in detail in commonly assigned U.S. Pat. No. 4,548, 209 "Energy Converter for Implantable Cardioverter" to Wielders, et al. Proper charging polarities are maintained by diodes 170, 172, 174 and 176 interconnecting the output windings of high-voltage transformer 168 and the capacitors 156, 158, 160, and 162. As noted above, the state of capacitor charge is monitored by circuitry within the high voltage output circuit 140 that provides a VCAP, feedback signal indicative of the voltage to the timing and control circuit 144. Timing and control circuit 144 terminates the high voltage charge command HVCHG when the VCAP signal matches the programmed capacitor output voltage, i.e., the cardioversion-defibrillation peak shock voltage.

Control circuit 144 then develops first and second control signals NPULSE 1 and NPULSE 2, respectively, that are applied to the high voltage output circuit 140 for triggering the delivery of cardioverting or defibrillating shocks. In particular, the NPULSE 1 signal triggers discharge of the first capacitor bank, comprising capacitors 156 and 158. The NPULSE 2 signal triggers discharge of the first capacitor bank and a second capacitor bank, comprising capacitors 160 and 162. It is possible to select between a plurality of output pulse regimes simply by modifying the number and time order of assertion of the NPULSE 1 and NPULSE 2 signals. The NPULSE 1 signals and NPULSE 2 signals may be provided sequentially, simultaneously or individually. In this way, control circuitry 144 serves to control operation of the high voltage output stage 140, which delivers high energy cardioversion-defibrillation shocks between the pair of the cardioversion-defibrillation electrodes 113 and 123 coupled to the HV-1 and COMMON output as shown in FIG. 3.

Thus, subcutaneous device 14 monitors the patient's cardiac status and initiates the delivery of a cardioversion-defibrillation shock through the cardioversion-defibrillation electrodes 24 and 28 in response to detection of a tachyarrhythmia requiring cardioversion-defibrillation. The high HVCHG signal causes the high voltage battery 112 to be connected through the switch circuit 114 with the high voltage charge circuit 164 and the charging of output capacitors 156, 158, 160, and 162 to commence. Charging continues until the programmed charge voltage is reflected by the VCAP signal, at which point control and timing circuit 144 sets the HVCHG signal low terminating charging and opening switch circuit 114. Typically, the charging cycle takes only fifteen to twenty seconds, and occurs very infrequently. The subcutaneous device 14 can be programmed to attempt to deliver cardioversion shocks to the heart in the manners described above in timed synchrony with a detected R-wave or can be programmed or fabricated to deliver defibrillation shocks to the heart in the manners described above without attempting to synchronize the delivery to a detected R-wave. Episode data related to the detection of the tachyarrhythmia and delivery of the cardioversion-defibrillation shock can be stored in RAM for uplink telemetry transmission to an external programmer as is well known in the art to facilitate in diagnosis of the patient's cardiac state. A patient receiving the device 14 on a prophylactic basis would be instructed to report each such episode to the attending physician for further evaluation of the patient's condition and assessment for the need for implantation of a more sophisticated ICD.

Subcutaneous device 14 desirably includes telemetry circuit (not shown in FIG. 3), so that it is capable of being programmed by means of external programmer 20 via a 2-way telemetry link 22 (shown in FIG. 1). Uplink telemetry allows device status and diagnostic/event data to be sent to external programmer 20 for review by the patient's physician. Downlink telemetry allows the external programmer via physician control to allow the programming of device function and the optimization of the detection and therapy for a specific patient. Programmers and telemetry systems suitable for use in the practice of the present invention have been well known for many years. Known programmers typically communicate with an implanted device via a bidirectional radio-frequency telemetry link, so that the programmer can transmit control commands and operational parameter values to be received by the implanted device, so that the implanted device can communicate diagnostic and operational data to the programmer. Programmers believed to be suitable for the purposes of practicing the present invention include the Models 9790 and CareLink® programmers, commercially available from Medtronic, Inc., Minneapolis, Minn.

Various telemetry systems for providing the necessary communications channels between an external programming unit and an implanted device have been developed and are well known in the art. Telemetry systems believed to be suitable for the purposes of practicing the present invention are disclosed, for example, in the following U.S. Patents: U.S. Pat. No. 5,127,404 to Wyborny et al. entitled "Telemetry Format for Implanted Medical Device"; U.S. Pat. No. 4,374, 382 to Markowitz entitled "Marker Channel Telemetry System for a Medical Device"; and U.S. Pat. No. 4,556,063 to Thompson et al. entitled "Telemetry System for a Medical Device". The Wyborny et al. '404, Markowitz '382, and Thompson et al. '063 patents are commonly assigned to the assignee of the present invention, and are each hereby incorporated by reference herein in their respective entireties.

Figure 4:
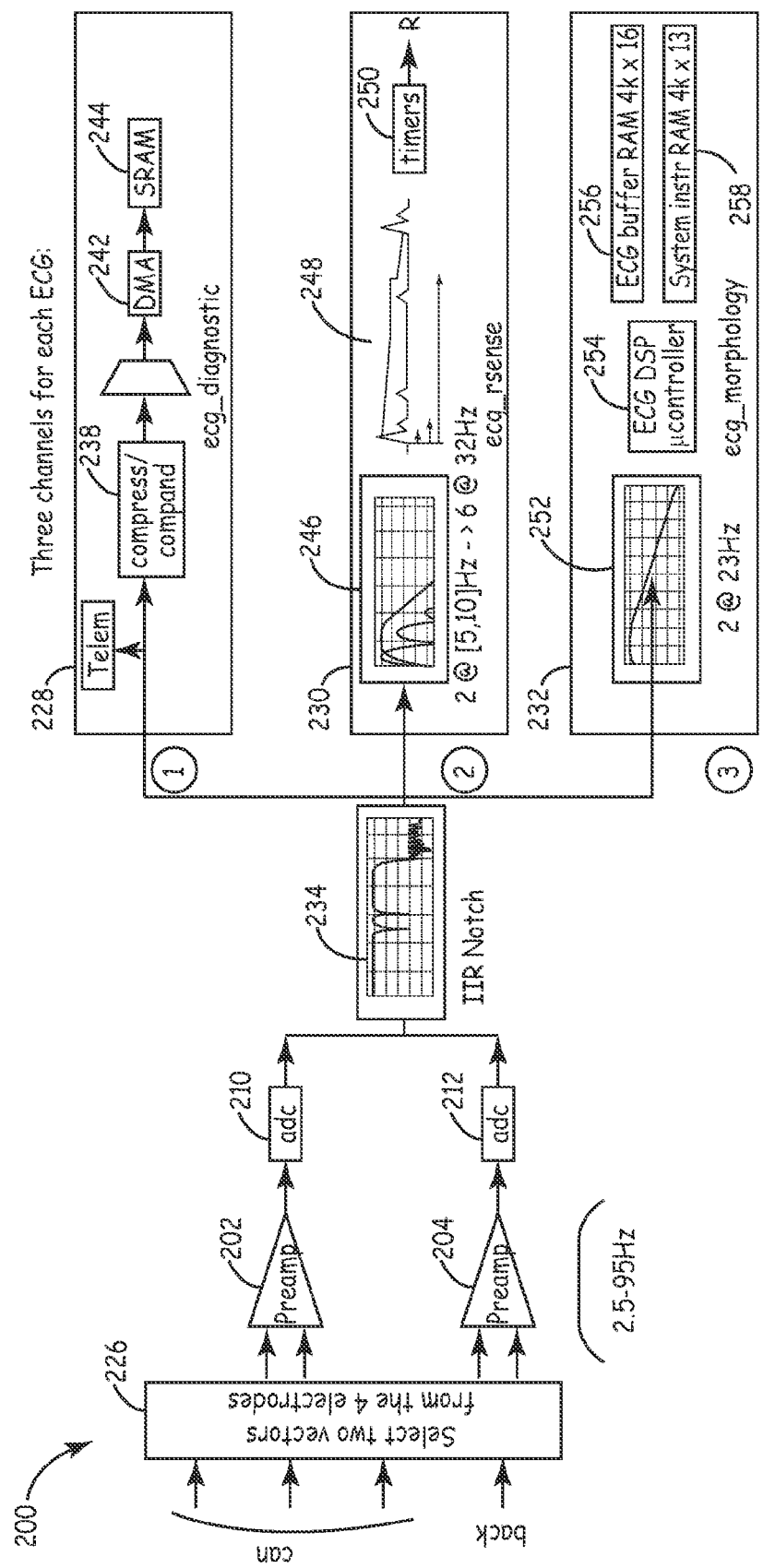
FIG. 4 is a schematic diagram of signal processing aspects of a subcutaneous device according to an exemplary embodiment of the present invention.

FIG. 4 is a schematic diagram of signal processing aspects of a subcutaneous device according to an exemplary embodiment of the present invention. The transthoracic ECG signal (ECG1) detected between the distal electrode 26 of subcutaneous lead 18 and one of electrodes 28 positioned on the subcutaneous device 14 are amplified and bandpass filtered (2.5-105 Hz) by pre-amplifiers 202 and 206 located in Sense Amp 190 of FIG. 3. The amplified EGM signals are directed to A/D converters 210 and 212, which operate to sample the time varying analog EGM signal and digitize the sampled points. The digital output of A/D converters 210 and 212 are applied to temporary buffers/control logic, which shifts the digital data through its stages in a FIFO manner under the control of Pacer/Device Timing block 178 of FIG. 3. Virtual Vector block 226 selects one housing-based ECG signal (ECG2) from any pair of electrodes 28 as described, for example, in U.S. Pat. No. 5,331,966 "Subcutaneous Multi-Electrode Sensing System, Method and Pacer" to Bennett, et al or, alternatively, generates a virtual vector signal under control of Microprocessor 142 and Control block 144 as described in U.S. Pat. No. 6,505,067 "System and Method for Deriving Virtual ECG or EGM Signal" to Lee, et al; both patents incorporated herein by reference in their entireties. ECG1 and ECG2 vector selection may be selected by the patient's physician and programmed via telemetry link 22 from programmer 20.

According to an embodiment of the present invention, in order to automatically select the preferred ECG vector set, it is necessary to have an index of merit upon which to rate the quality of the signal. "Quality" is defined as the signal's ability to provide accurate heart rate estimation and accurate morphological waveform separation between the patient's usual sinus rhythm and the patient's ventricular tachyarrhythmia.

Appropriate indices may include R-wave amplitude, R-wave peak amplitude to waveform amplitude between R-waves (i.e., signal to noise ratio), low slope content, relative high versus low frequency power, mean frequency estimation, probability density function, or some combination of these metrics.

Automatic vector selection might be done at implantation or periodically (daily, weekly, monthly) or both. At implant, automatic vector selection may be initiated as part of an automatic device turn-on procedure that performs such activities as measure lead impedances and battery voltages. The device turn-on procedure may be initiated by the implanting physician (e.g., by pressing a programmer button) or, alternatively, may be initiated automatically upon automatic detection of device/lead implantation. The turn-on procedure may also use the automatic vector selection criteria to determine if ECG vector quality is adequate for the current patient and for the device and lead position, prior to suturing the subcutaneous device 14 in place and closing the incision. Such an ECG quality indicator would allow the implanting physician to maneuver the device to a new location or orientation to improve the quality of the ECG signals as required. The preferred ECG vector or vectors may also be selected at implant as part of the device turn-on procedure. The preferred vectors might be those vectors with the indices that maximize rate estimation and detection accuracy. There may also be an a priori set of vectors that are preferred by the physician, and as long as those vectors exceed some minimum threshold, or are only slightly worse than some other more desirable vectors, the a priori preferred vectors are chosen. Certain vectors may be considered nearly identical such that they are not tested unless the a priori selected vector index falls below some predetermined threshold.

Depending upon metric power consumption and power requirements of the device, the ECG signal quality metric may be measured on the range of vectors (or alternatively, a subset) as often as desired. Data may be gathered, for example, on a minute, hourly, daily, weekly or monthly basis. More frequent measurements (e.g., every minute) may be averaged over time and used to select vectors based upon susceptibility of vectors to occasional noise, motion noise, or EMI, for example.

Alternatively, the subcutaneous device 14 may have an indicator/sensor of patient activity (piezo-resistive, accelerometer, impedance, or the like) and delay automatic vector measurement during periods of moderate or high patient activity to periods of minimal to no activity. One representative scenario may include testing/evaluating ECG vectors once daily or weekly while the patient has been determined to be asleep (using an internal clock (e.g., 2:00 am) or, alternatively, infer sleep by determining the patient's position (via a 2- or 3-axis accelerometer) and a lack of activity).

If infrequent automatic, periodic measurements are made, it may also be desirable to measure noise (e.g., muscle, motion, EMI, etc.) in the signal and postpone the vector selection measurement when the noise has subsided.

Subcutaneous device 14 may optionally have an indicator of the patient's posture (via a 2- or 3-axis accelerometer). This sensor may be used to ensure that the differences in ECG quality are not simply a result of changing posture/position. The sensor may be used to gather data in a number of postures so that ECG quality may be averaged over these postures or, alternatively, selected for a preferred posture.

In the preferred embodiment, vector quality metric calculations would occur a number of times over approximately 1 minute, once per day, for each vector. These values would be averaged for each vector over the course of one week. Averaging may consist of a moving average or recursive average depending on time weighting and memory considerations. In this example, the preferred vector(s) would be selected once per week.

Continuing with FIG. 4, a diagnostic channel 228 receives a programmable selected ECG signal from the housing based subcutaneous electrodes and the transthoracic ECG from the distal electrode 26 on lead 18. Block 238 compresses the digital data, the data is applied to temporary buffers/control logic 218 which shifts the digital data through its stages in a FIFO manner under the control of Pacer/Device Timing block 178 of FIG. 3, and the data is then stored in SRAM block 244 via direct memory access block 242.

The two selected ECG signals (ECG1 and ECG2) are additionally used to provide R-wave interval sensing via ECG sensing block 230. IIR notch filter block 246 provides 50/60 Hz notch filtering. A rectifier and auto-threshold block 248 provides R-wave event detection as described in U.S. Pat. No. 5,117,824 "Apparatus for Monitoring Electrical Physiologic Signals" to Keimel, et al; publication WO2004023995 "Method and Apparatus for Cardiac R-wave Sensing in a Subcutaneous ECG Waveform" to Cao, et al and U.S. Publication No. 2004/0260350 "Automatic EGM Amplitude Measurements During Tachyarrhythmia Episodes" to Brandstetter, et al, all incorporated herein by reference in their entireties. The rectifier of block 248 performs full wave rectification on the amplified, narrowband signal from bandpass filter 246. A programmable fixed threshold (percentage of peak value), a moving average or, more preferably, an auto-adjusting threshold is generated as described in the '824 patent or '350 publication. In these references, following a detected depolarization, the amplifier is automatically adjusted so that the effective sensing threshold is set to be equal to a predetermined portion of the amplitude of the sensed depolarization, and the effective sensing threshold decays thereafter to a lower or base-sensing threshold. A comparator in block 248 determines signal crossings from the rectified waveform and auto-adjusting threshold signal. A timer block 250 provides R-wave to R-wave interval timing for subsequent arrhythmia detection (to be described herein below). The heart rate estimation is derived from the last 12 R-R intervals (e.g., by a mean, trimmed mean, or median, for example), with the oldest data value being removed as a new data value is added.

Figure 5:
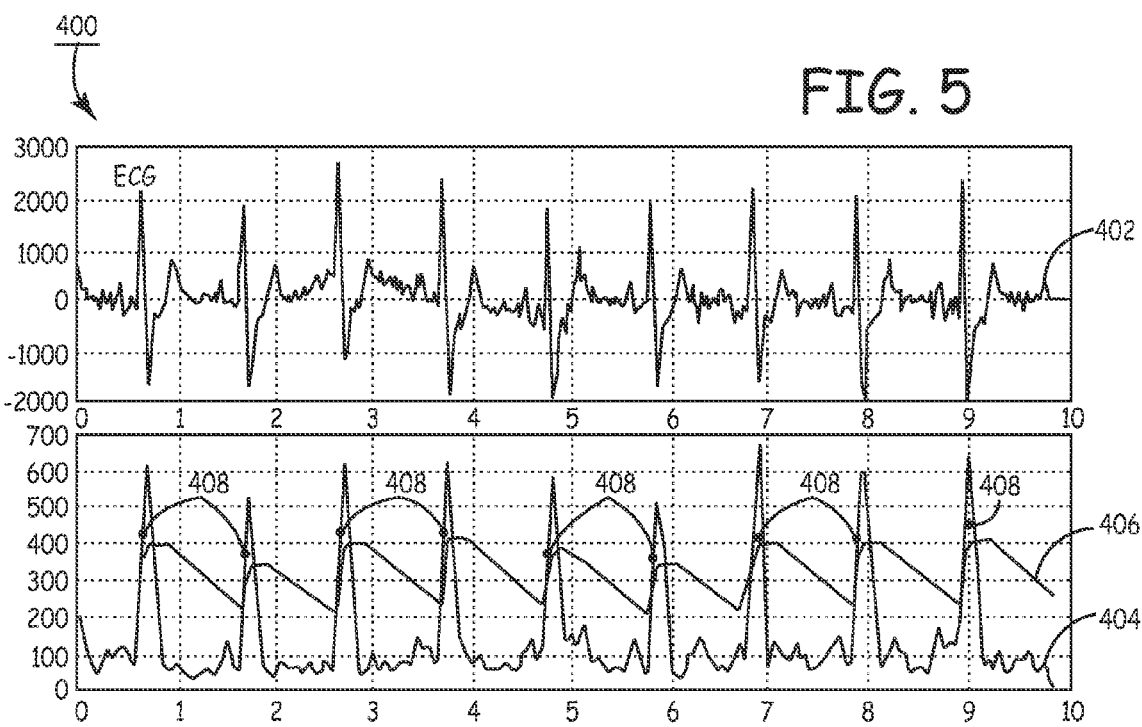
FIG. 5 is a state diagram of detection of arrhythmias in a subcutaneous device according to an embodiment of the present invention.

FIG. 5 is a schematic diagram of a rectifier and auto-threshold unit in a subcutaneous device according to an embodiment of the present invention. Waveform 402 depicts a typical subcutaneous ECG waveform and waveform 404 depicts the same waveform after filtering and rectification. A time dependant threshold 406 allows a more sensitive sensing threshold temporally with respect to the previous sensed R-wave. Sensed events 408 indicate when the rectified ECG signal 404 exceeds the auto-adjusting threshold and a sensed event has occurred.

Returning to FIG. 4, the subcutaneous ECG signal (ECG1) is applied to ECG morphology block 232, filtered by a 2-pole 23 Hz low pass filter 252 and evaluated by DSP microcontroller 254 under control of program instructions stored in System Instruction RAM 258. ECG morphology is used for subsequent rhythm detection/determination (to be described herein below).

Figure 6:
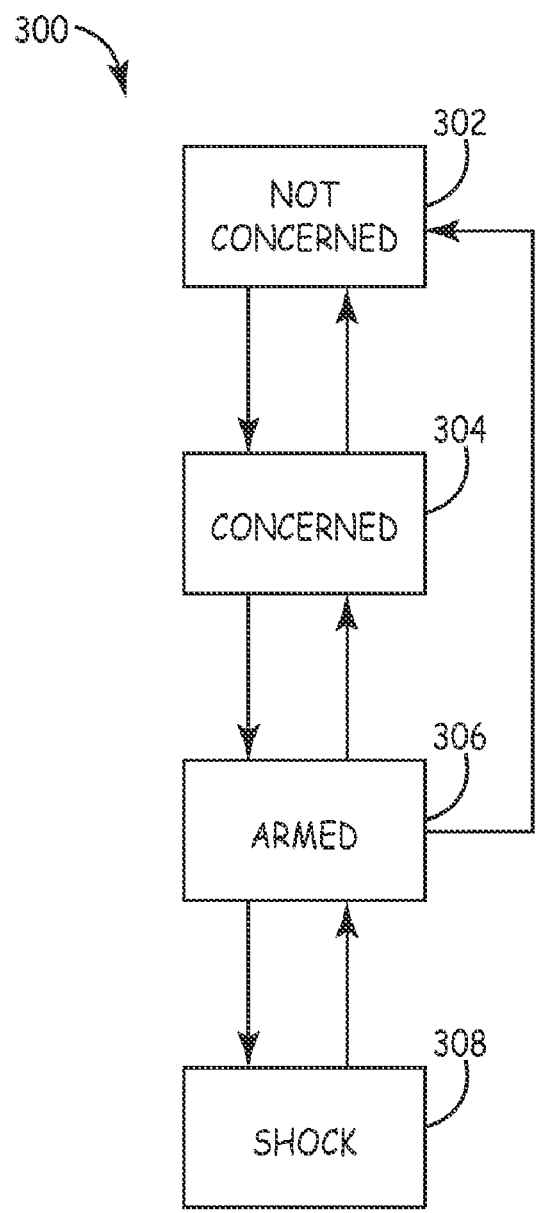
FIG. 6 is a flow chart of a method for detecting arrhythmias in a subcutaneous device according to an embodiment of the present invention.

FIG. 6 is a state diagram of detection of arrhythmias in a medical device according to an embodiment of the present invention. As illustrated in FIG. 6, during normal operation, the device 14 is in a not concerned state 302, described in more detail herein below, during which R-wave intervals are being evaluated to identify periods of rapid rates and/or the presence of asystole. Upon detection of short R-wave intervals simultaneously in both ECG leads, indicative of an event that, if confirmed, may require the delivery of therapy, the device 14 transitions from the not concerned state 302 to a concerned state 304, described in more detail herein below. In the concerned state 304 the device 14 evaluates a predetermined window of ECG signals to determine the likelihood that the signal is corrupted with noise and to discriminate rhythms requiring shock therapy from those that do not require shock therapy, using a combination of R-wave intervals and ECG signal morphology information.

If a rhythm requiring shock therapy continues to be detected while in the concerned state 304, the device 14 transitions from the concerned state 304 to an armed state 306, described in more detail herein below. If a rhythm requiring shock therapy is no longer detected while the device is in the concerned state 304 and the R-wave intervals are determined to no longer be short, the device 14 returns to the not concerned state 302. However, if a rhythm requiring shock therapy is no longer detected while the device is in the concerned state 304, but the R-wave intervals continue to be detected as being short, processing continues in the concerned state 304.

In the armed state 306, the device 14 charges the high voltage shocking capacitors and continues to monitor R-wave intervals and ECG signal morphology for spontaneous termination. If spontaneous termination of the rhythm requiring shock therapy occurs, the device 14 returns to the not concerned state 302. If the rhythm requiring shock therapy is still determined to be occurring once the charging of the capacitors is completed, the device 14 transitions from the armed state 306 to a shock state 308, described in more detail herein below.

In the shock state 308, the device 14 delivers a shock and returns to the armed state 306 to evaluate the success of the therapy delivered.

Figure 7A:
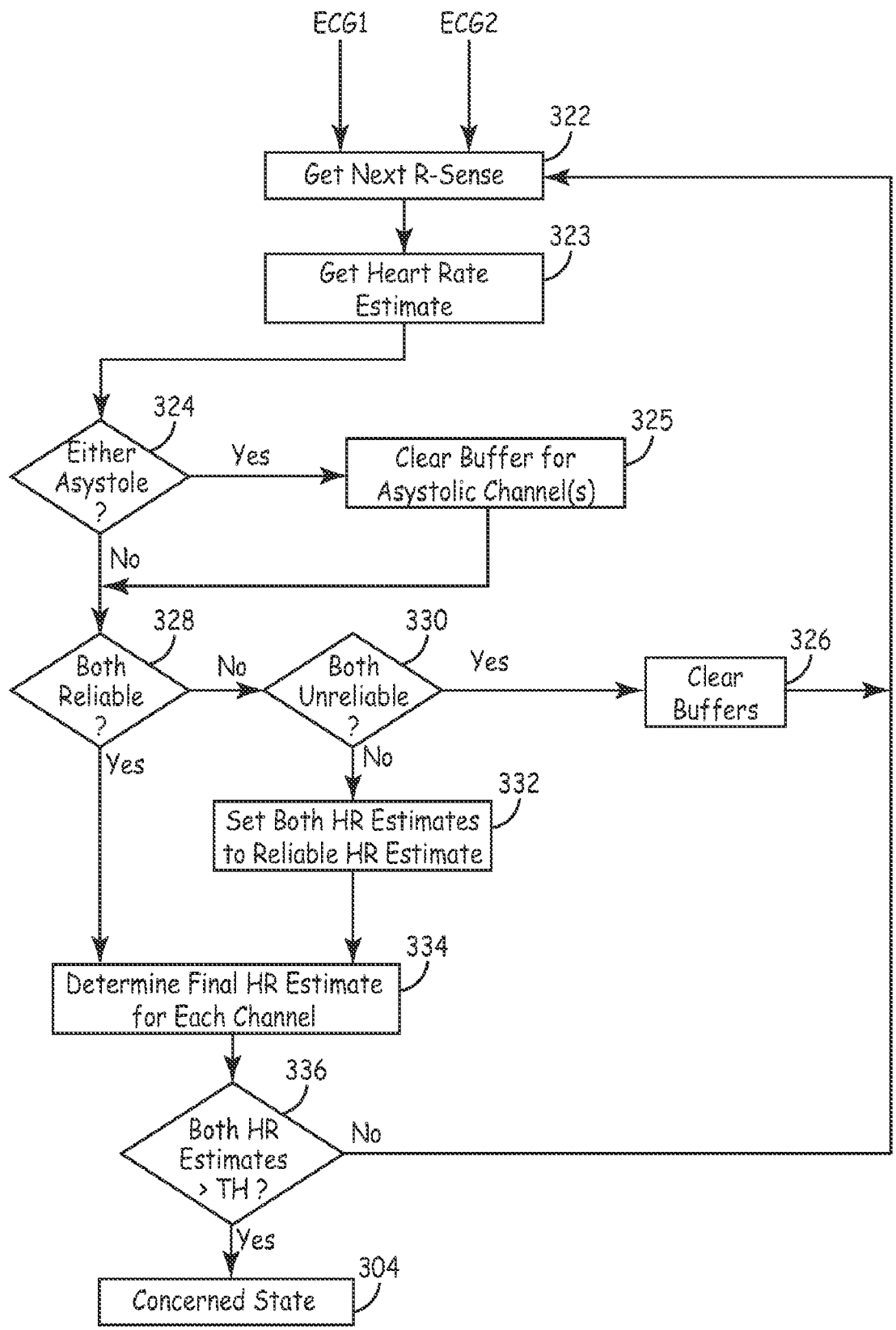
FIGS. 7A-7J are flow charts of a method for detecting arrhythmias in a subcutaneous device according to an embodiment of the present invention.

FIGS. 7A-7I are flow charts of a method for detecting arrhythmias in a subcutaneous device according to an embodiment of the present invention. As illustrated in FIG. 7A, device 14 continuously evaluates the two channels ECG1 and ECG2 associated with two predetermined electrode vectors to when sensed events occur. For example, the electrode vectors for the two channels ECG1 and ECG2 may include a horizontal vector selected between two of the electrodes 28 (ECG2) located along the housing of the device 14 as one electrode vector, while the other electrode vector is a front to back vector selected between the distal electrode 26 (ECG1) and one of the subcutaneous electrodes 28, for example. The input signal from each channel ECG1 and ECG2 is pre-processed and rectified, and an adaptive auto-adjusting threshold is then applied. According to an embodiment of the present invention, a sensed event is determined to have occurred, for example, whenever the rising edge of the filtered ECG crosses the threshold.

Figure 8:
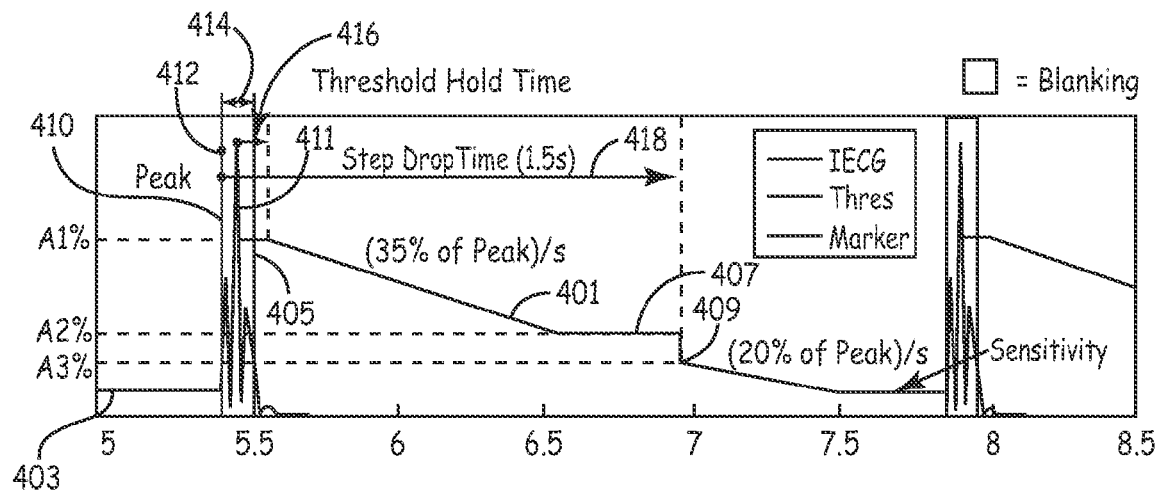
FIG. 8 is a graphical representation of sensing of cardiac activity according to an embodiment of the present invention.

FIG. 8 is a graphical representation of sensing of cardiac activity according to an embodiment of the present invention. In particular, the present invention utilizes an adaptive auto-adjusting threshold 401 during the R-wave sensing of Block 322 that includes a first threshold level 403, a second threshold level 405, a third threshold level 407 and a fourth threshold level 409. An example of an auto-adjusting threshold is described, for example, in commonly assigned U.S. Patent Application Publication No. 2004/0049120, to Cao et al., filed Sep. 11, 2002, incorporated herein by reference in its entirety. Once there is a sensed event, which occurs whenever the rising edge of the rectified filtered ECG 411 crosses the threshold level, in this case threshold 403, indicated by marker 410, the threshold 401 is adjusted to the second threshold level 405, which is a first predetermined percentage of a peak amplitude 412 of the rectified filtered ECG 411, such as 65 percent, for example.

A blanking period 414 (nominally 150 ms, for example) prevents double counting of R-waves. During blanking period 414, the threshold 401 continues to track the predetermined percentage of rectified filtered ECG 411 until peak 412 is detected. Threshold 401 is held at the second threshold level 405 during a threshold hold time period 416 (nominally 100 ms, for example) starting from the peak 412 location to prevent T-wave oversensing by delaying the linear decay. Threshold 401 then decays at a first predetermined rate, such as 35% of peak 412 per second, for example, until threshold 401 reaches the third threshold level 407, which is a second predetermined percentage of peak amplitude 412 (nominally 30%, for example). Threshold 401 is held at the third threshold level 407 until a step drop time 418 from the sensed event 410 (1.5 sec, for example) has expired. Once the step drop time 418 has expired, the threshold 401 is instantaneously set at the fourth threshold level 409 and begins to decay at a second predetermined rate, such as 20% of peak 412 per second, for example. The threshold 401 continues to decay linearly at the second predetermined rate until the threshold 401 reaches the first threshold level 403. At no time can the threshold 401 become less than the first threshold level 403.

The step drop time 418 allows abrupt adjustment of the threshold 401 in order to accommodate sensing of sudden reductions in R-wave amplitudes. The second predetermined rate associated with the linear decay is set at a rate that prevents oversensing of P-waves while maintaining adequate decay for sensing sudden drops in R-waves. If, at any time throughout this threshold adjustment process, a sensed event re-occurs outside blanking period 414, then the threshold 401 is adjusted to the second threshold level 405, and the threshold adjustment process is repeated.

According to an embodiment of the present invention, the nominal settings for the R-wave detector parameters may be set, for example, with the first threshold level being 25 microvolts, the second threshold level, third threshold level and fourth threshold level being set as 65, 30 and 20 percent of the peak amplitude 412, respectively, blanking period 414 being set as 150 milliseconds, threshold hold time 416 being set as 100 milliseconds, and a maximum threshold level being 650 microvolts. These nominal settings may differ between the anterior housing-based bipolar ECG and the front to back ECG in order to account for the expected difference in amplitude and noise characteristics for those vectors.

The R-wave sensing described above is applied to each ECG channel ECG1 and ECG2 independently. According to the present invention, sensing of ventricular events on either channel will trigger execution of state machine in states 1 and 4. During states 2 and 3, R-wave sensing continues but state machine is triggered every predetermined number of seconds, as described below.

Returning to FIG. 7A, a buffer of the most recent 12 R-R intervals obtained during R-wave processing using the sensing scheme of FIG. 8, described above, for example, is independently maintained for each of the two sensing channels ECG1 and ECG2. When the next sensed R-wave is obtained, Block 322, which initially would be the $12^{th}$ R-wave interval, a heart rate estimate is determined, Block 323, using a metric of heart rate, such as the mean, trimmed mean, or median of the RR intervals, for example. According to an embodiment of the present invention, the 9$^{th}$ fastest beat of the 12 beats on a beat by beat basis is utilized as the heart rate metric. Using the 9$^{th}$ fastest beat provides an estimate of heart rate that is less susceptible to oversensing while maintaining reasonable sensitivity to short R-R intervals as in the case of VT/VF. If the buffer of 12 R-R intervals contains any unknown R-R intervals (i.e., because the buffer is not yet filled) the initial estimate of heart rate is unknown.

Once the heart rate estimate is obtained using the heart rate metric, a determination is made as to whether asystole is detected for either channel, ECG1 or ECG 2, Block 324. According to an embodiment of the present invention, asystole is detected for the channel, for example, either by determining whether one of the 12 R-R intervals is greater than a predetermined time period, such as three seconds, for example, or if the time since the most recently sensed R wave exceeds a predetermined time period, such as three seconds, for example. The latter can occur if an R-wave is sensed, for example, in one channel ECG1, but the other channel ECG2 has not had an R-wave sense in three or more seconds. If asystole is detected for either of the two channels ECG1 or ECG2, the current 12 R-R intervals for channels that are determined to be in asystole are cleared from the buffers, Block 325, and the process continues by determining whether the current heart rate estimate is reliable for both channels ECG1 and ECG2, Block 328, described below.

If asystole is not detected for either channel ECG1 and ECG2, NO in Block 324, a determination is made independently for both channels ECG1 and ECG2 as to whether the current heart rate estimate for both channels ECG1 and ECG2 is reliable, Block 328. According to an embodiment of the present invention, the current heart rate estimate for each of the two channels ECG1 and ECG2 is determined not to be reliable, No in Block 328, if either there are unknown or cleared entries in the buffer for that channel, or if a predetermined number of the sensed R-waves associated with the current 12 R-R intervals for that channel was sensed at the minimum sensing threshold level, i.e., the first threshold level 403 of FIG. 8, for example, and if the current heart rate estimate for the channel is less than the programmed heart rate threshold. According to one embodiment, the predetermined number of sensed R-waves that must be sensed at the minimum threshold is set at two, for example. In addition, the programmed heart rate threshold may be within a range of 150 to 240 beats per minute, and is nominally set at 180 beats per minute, for example. It is understood that while the processing is described using a buffer of 12 R-R intervals, any number of intervals and predetermined number of sensed R-waves that must be sensed at the minimum threshold may be utilized.

If the above analysis does not determine that both of the channels are reliable, No in Block 328, a determination is made as to whether just one of the channels was unreliable or if both channels were unreliable, Block 330. If both channels are determined to be unreliable, the current 12 R-R intervals for both channels ECG1 and ECG2 are cleared from the buffers, Block 326, and the next R-sense is obtained for each channel, Block 322 using the sensing scheme of FIG. 8, described above, so that a new heart rate estimate is determined, Block 323, based on the new R-R intervals.

If only one channel is determined to unreliable, the value for the heart rate estimate for both channels is set to the current heart rate estimate for the channel determined to be reliable, Block 332. Once either both channels are determined to be reliable, YES in Block 328, or only one of the two channels is determined to be unreliable and therefore the heart rate estimate for both channels is set to the current heart rate estimate for the channel determined to be reliable, Block 332, the final heart rate estimate is determined for each channel ECG1 and ECG2 based on those results, Block 334, i.e., the heart rate estimate for each channel is set equal to their respective heart rate estimates determined in Block 323, or both are set equal to the heart rate estimate associated with the channel determined to be reliable, Block 332. A determination is then made as to whether the final heart rate estimates for both channels is greater than a predetermined VT/VF threshold, Block 336. According to an embodiment of the present invention, the predetermined VTNF threshold of Block 336 is set at 180 bpm, for example, although any desired threshold could be utilized.

If the final heart rate estimates for one or both channels is not greater than the predetermined VT/VF threshold, the buffer containing the 12 R-R intervals for the channel not greater than the predetermined VT/VF threshold is updated by removing the first R-sense, shifting the remaining eleven R-sense samples back so that the second R-sense becomes the first R-sense, and so forth, and inserting the next detected R-sense, Block 322, as the twelfth R-sense for each corresponding channel ECG1 and ECG2. A new current heart rate estimate is then determined, Block 323. Once the final heart rate estimates for both channels is greater than the predetermined VT/VF threshold, Yes in Block 336, the process transitions from the not concerned state 302 to the concerned state 304.

According to the present invention, upon transition from the not concerned state 302 to the concerned state 304, Block 305, a most recent window of ECG data from both channels ECG1 and ECG2 are utilized, such as three seconds, for example, so that processing is triggered in the concerned state 304 by a three-second timeout, rather than by the sensing of an R-wave, which is utilized when in the not concerned state 302, described above. It is understood that while the processing is described as being triggered over a three second period, other times periods for the processing time utilized when in the concerned state 304 may be chosen, but should preferably be within a range of 0.5 to 10 seconds. As a result, although sensing of individual R-waves continues to occur in both channels ECG1 and ECG2 when in the concerned state 304, and the buffer of 12 R-R intervals continues to be updated, the opportunities for changing from the concerned state 304 to another state and the estimates of heart rate only occur once the three-second timer expires. Upon initial entry to the concerned state 304, it is advantageous to process the most recent three-seconds of ECG data, i.e., ECG data for the three seconds leading up to the transition to the concerned state 304. This requires a continuous circular buffering of the most recent three seconds of ECG data even while in the not concerned state 302.

Figure 7B:
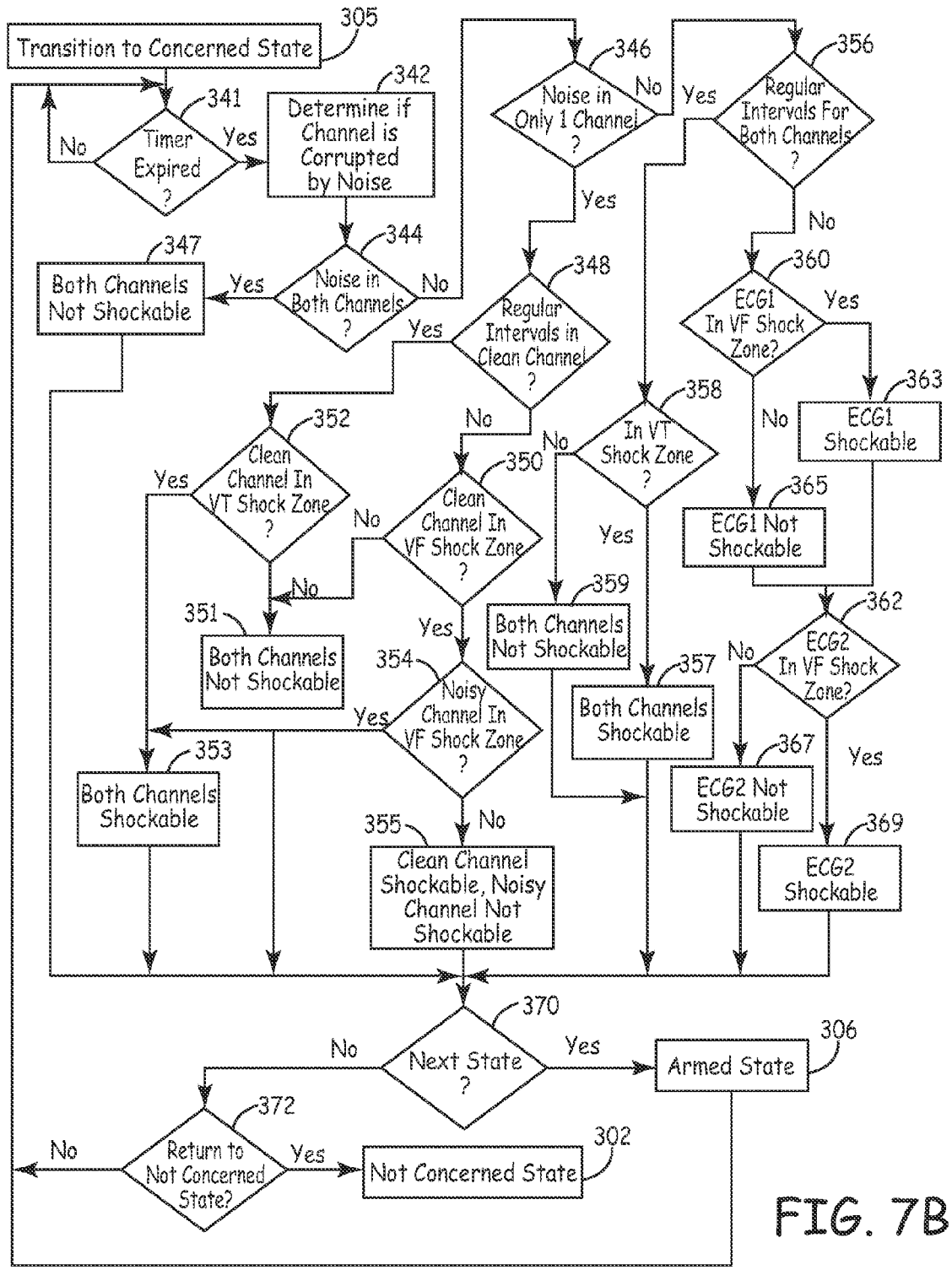

As described in detail below, while in the concerned state 304, the present invention determines how sinusoidal and how noisy the signals are in order to determine the likelihood that a ventricular fibrillation (VF) or fast ventricular tachycardia (VT) event is taking place, since the more sinusoidal and low noise the signal is, the more likely a VT/VF event is taking place. As illustrated in FIG. 7B, once the device transitions from the not concerned state 302 to the concerned state 304, Block 305, a buffer for each of the two channels ECG1 and ECG2 for storing classifications of 3-second segments of data as "shockable" or "non-shockable" is cleared. Processing of signals of the two channels ECG1 and ECG2 while in the concerned state 304 is then triggered by the three second time period, rather than by the sensing of an R-wave utilized during the not concerned state 302, described above.

Once the three second time interval has expired, YES in Block 341, morphology characteristics of the signal during the three second time interval for each channel are utilized to determine whether the signals are likely corrupted by noise artifacts and to characterize the morphology of the signal as "shockable" or "not shockable". For example, using the signals associated with the three second time interval, a determination is made for each channel ECG1 and ECG2 as to whether the channel is likely corrupted by noise, Block 342, and a determination is then made as to whether both channels ECG1 and ECG2 are corrupted by noise, Block 344.

Figure 7C:
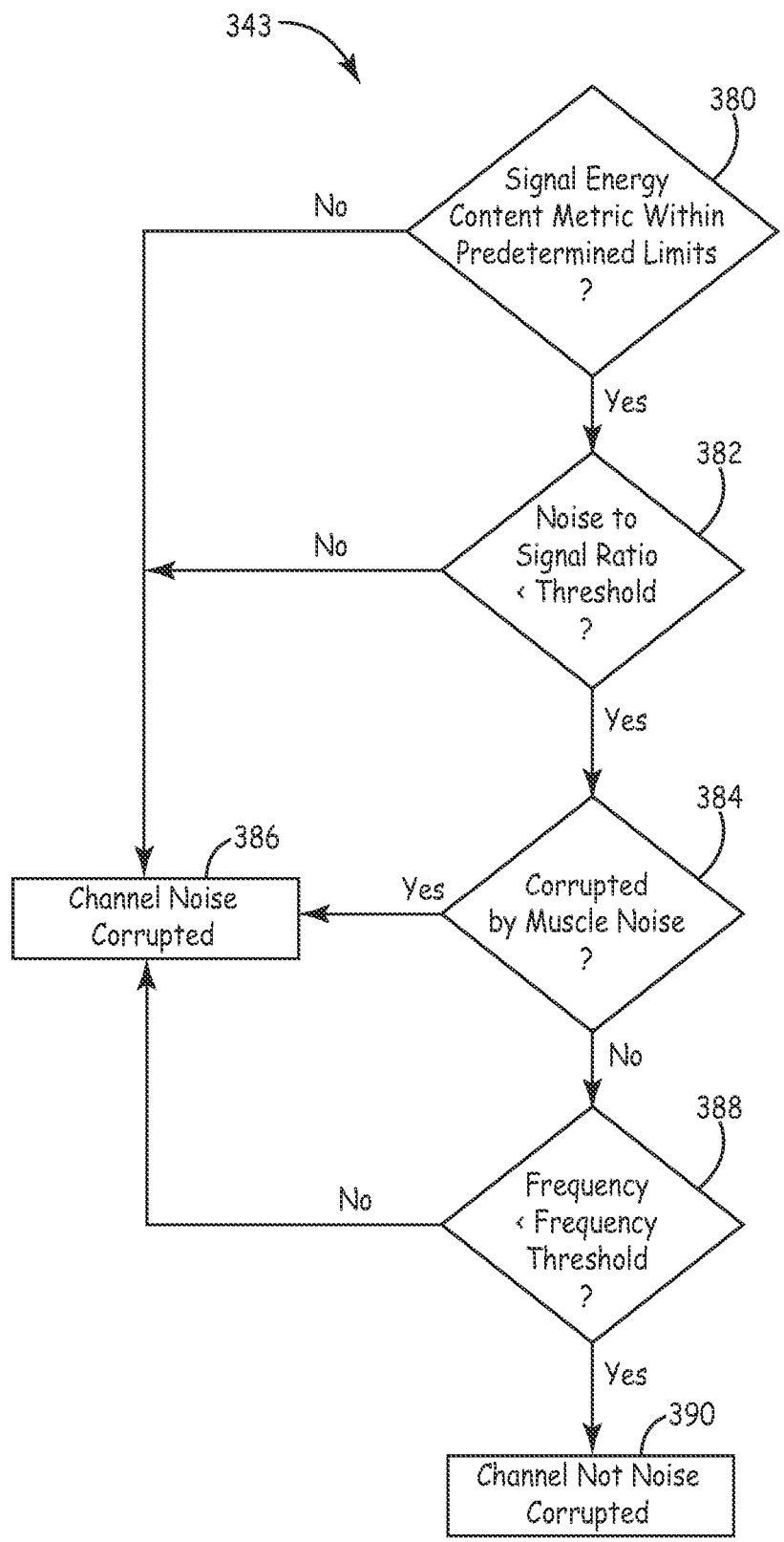

As illustrated in FIG. 7C, the determination as to whether the signal associated with each of the channels ECG1 and ECG2 is likely corrupted by noise, Block 342 of FIG. 7B, includes multiple sequential noise tests that are performed on each channel ECG and ECG2. During a first noise test, for example, a determination is made as to whether a metric of signal energy content of the signal for the channel is within predetermined limits, Block 380. For example, the amplitude of each sample associated with the three second window is determined, resulting in N sample amplitudes, from which a mean rectified amplitude is calculated as the ratio of the sum of the rectified sample amplitudes to the total number of sample amplitudes N for the segment. If the sampling rate is 256 samples per second, for example, the total number of sample amplitudes N for the three-second segment would be N=768 samples.

Once the mean rectified amplitude is calculated, a determination is made as to whether the mean rectified amplitude is between an upper average amplitude limit and a lower average amplitude limit, the lower average amplitude limit being associated with asystole episodes without artifact and the upper average amplitude limit being associated with a value greater than what would be associated with ventricular tachycardia and ventricular fibrillation events. According to an embodiment of the present invention, the upper average amplitude limit is set as 1.5 mV, and the lower average amplitude limit is set as 0.013 mV. While the metric of signal energy content is described above as the mean rectified amplitude, it is understood that other signal of energy contents could be utilized.

If the determined mean rectified amplitude is not between the upper average amplitude limit and the lower average amplitude limit, the three second segment for that channel is identified as being likely corrupted with noise, Block 386, and no further noise tests are initiated for that channel's segment.

If the determined mean rectified amplitude is located between the upper average amplitude limit and the lower average amplitude limit, a noise to signal ratio is calculated and a determination is made as to whether the noise to signal ratio is less than a predetermined noise to signal threshold, Block 382. For example, the amplitude of each sample associated with the three second window is determined, resulting in N raw sample amplitudes. The raw signal is lowpass filtered, resulting in L lowpass sample amplitudes. The raw mean rectified amplitude is determined as the average of the absolute values of the raw sample amplitudes. The lowpass mean rectified amplitude is determined as the average of the absolute values of the lowpass sample amplitudes. Next, a highpass mean rectified amplitude is then calculated as the difference between the raw mean rectified amplitude and the lowpass mean rectified amplitude. The noise to signal ratio is then determined as the ratio of the highpass mean rectified amplitude to the lowpass mean rectified amplitude. If the noise to signal ratio is greater than a predetermined threshold, such as 0.0703, for example, the three second segment for that channel is identified as being likely corrupted with noise, Block 386, and no further noise tests are initiated for the segment.

If the noise to signal ratio is less than or equal to the predetermined threshold, a determination is made as to whether the signal is corrupted by muscle noise, Block 384. According to an embodiment of the present invention, the determination as to whether the signal is corrupted by muscle noise is made by determining whether the signal includes a predetermined number of signal inflections indicative of the likelihood of the signal being corrupted by muscle noise, using a muscle noise pulse count that is calculated to quantify the number of signal inflections in the three second interval for each channel ECG1 and ECG2. The presence of a significant number of inflections is likely indicative of muscle noise.

Figure 9A:
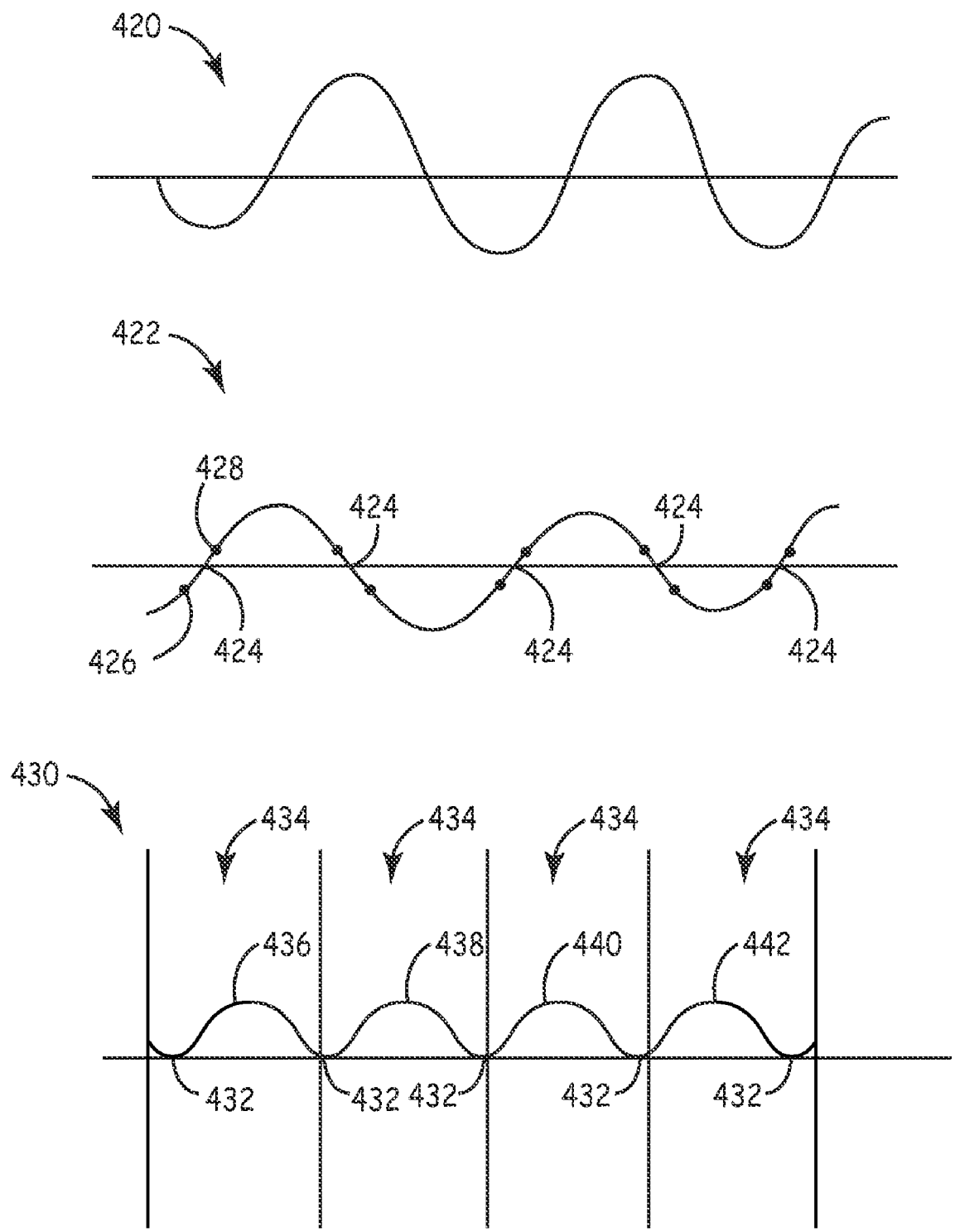
FIG. 9A is a graphical representation of a determination of whether a signal is corrupted by muscle noise according to an embodiment of the present invention.
Figure 9B:
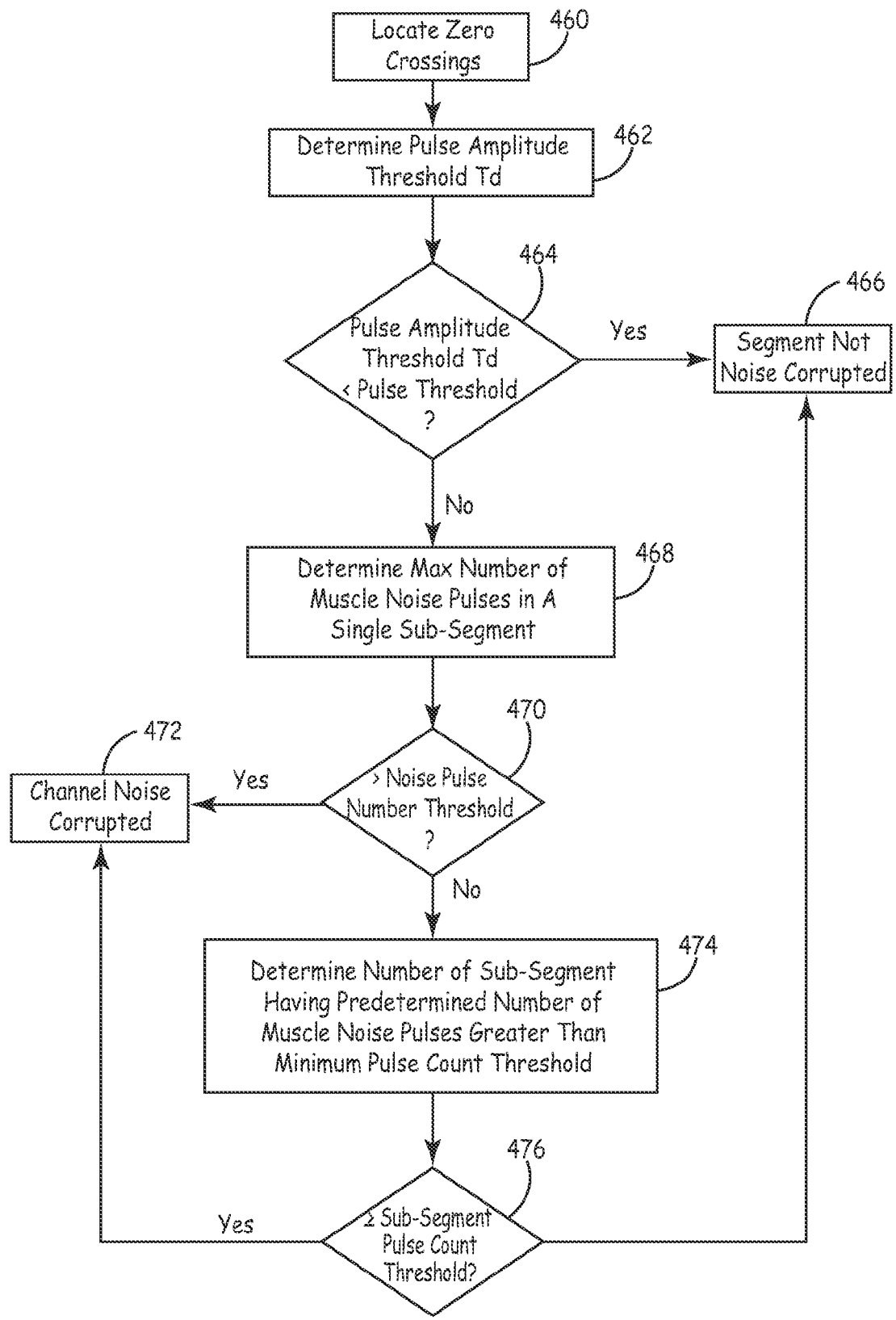
FIG. 9B is a flowchart of a method of determining whether a signal is corrupted by muscle noise according to an embodiment of the present invention.

FIG. 9A is a graphical representation of a determination of whether a signal is corrupted by muscle noise according to an embodiment of the present invention. FIG. 9B is a flowchart of a method of determining whether a signal is corrupted by muscle noise according to an embodiment of the present invention. For example, as illustrated in FIGS. 9A and 9B, in order to determine a muscle noise count for the three second interval, the raw signal 420 is applied to a first order derivative filter to obtain a derivative signal 422, and all of the zero-crossings 424 in the derivative signal 422 are located, Block 460. A data pair corresponding to the data points immediately prior to and subsequent to the zero crossings 424, points 426 and 428 respectively, for each crossing is obtained. The value of the data point in each data pair with smaller absolute value is zeroed in order to allow a clear demarcation of each pulse when a rectified signal 430 is derived from the derivative signal 422 with zeroed zero-crossing points 432.

A pulse amplitude threshold Td, for determining whether the identified inflection is of a significant amplitude to be identified as being associated with muscle noise, is determined, Block 462, by dividing the rectified signal from the three second segment into equal sub-segments 434, estimating a local maximum amplitude 436-442 for each of the sub-segments 434, and determining whether the local amplitudes 436-442 are less than a portion of the maximum amplitude, which is maximum amplitude 440 in the example of FIG. 9, for the whole three second segment. If the local maximum amplitude is less than the portion of the maximum amplitude for the whole three second segment, the local maximum amplitude is replaced by the maximum for the whole three second segment for the sub-segment corresponding to that local maximum amplitude.

It is understood that while only two or less zero-crossing points are shown as being located within the sub-segments in the illustration of FIG. 9 for the sake of simplicity, in fact each of the sub-segments 434, which have a length of approximately 750 milliseconds, will contain many inflections, such as every 25 milliseconds, for example.

According to an embodiment of the present invention, the three second segment is divided into four sub-segments and the local maximum amplitudes are replaced by the maximum amplitude for the whole segment if the local maximum amplitude is less than one fifth of the maximum amplitude for the whole segment. Once the determination of whether to replace the local maximum amplitudes for each of the sub-segments with the maximum amplitude for the whole segment is completed, the pulse amplitude threshold Td for the segment is set equal to a predetermined fraction of the mean of the local maximum amplitudes for each of the sub-segments. According to an embodiment of the present invention, the pulse amplitude threshold Td for the three second segment is set equal to one sixth of the mean of the local maximum amplitudes 436-440.

Once the pulse amplitude threshold Td has been determined, the inflections associated with the signal for the three second segment is classified as being of significant level to be likely indicative of noise by determining whether the pulse amplitude threshold Td is less than a pulse threshold, Block 464. According to an embodiment of the present invention, the pulse threshold is set as 1 microvolt. If the pulse amplitude threshold Td is less than the pulse threshold, the signal strength is too small for a determination of muscle noise, and therefore the signal is determined to be not likely corrupted by noise and therefore the channel is determined to be not noise corrupted, Block 466.

If the pulse amplitude threshold Td is greater than or equal to the pulse threshold, the three second segment is divided into twelve sub-segments of 250 ms window length, the number of muscle noise pulses in each sub-segment is counted, and both the sub-segment having the maximum number of muscle noise pulses and the number of sub-segments having 6 or more muscle noise pulses that are greater than a predetermined minimum threshold is determined. Muscle noise is determined to be present in the signal if either the maximum number of muscle noise pulses in a single sub-segment is greater than a noise pulse number threshold or the number of sub-segments of the twelve sub-segments having 6 or more muscle noise pulses greater than the minimum threshold is greater than or equal to a sub-segment pulse count threshold. According to an embodiment of the present invention, the noise pulse number threshold is set equal to eight and the sub-segment pulse count threshold is set equal to three.

For example, if the pulse amplitude threshold Td is greater than or equal to the pulse threshold, No in Block 464, the maximum number of muscle noise counts in a single sub-segment is determined, Block 468. If the maximum number of muscle noise counts is greater than the noise pulse number threshold, Yes in Block 470, the channel is determined to be noise corrupted, Block 472. If the maximum number of muscle noise counts for the channel is less than or equal to the noise pulse number threshold, No in Block 470, the number of sub-segments of the twelve sub-segments having 6 or more muscle noise pulses greater than the minimum threshold is determined, Block 474, and if the number is greater than or equal to a sub-segment pulse count threshold, Yes in Block 476, the channel is determined to be noise corrupted, Block 472. If the number is less than the sub-segment pulse count threshold, No in Block 476, the channel is determined not to be noise corrupted, Block 466.

Figure 9C:
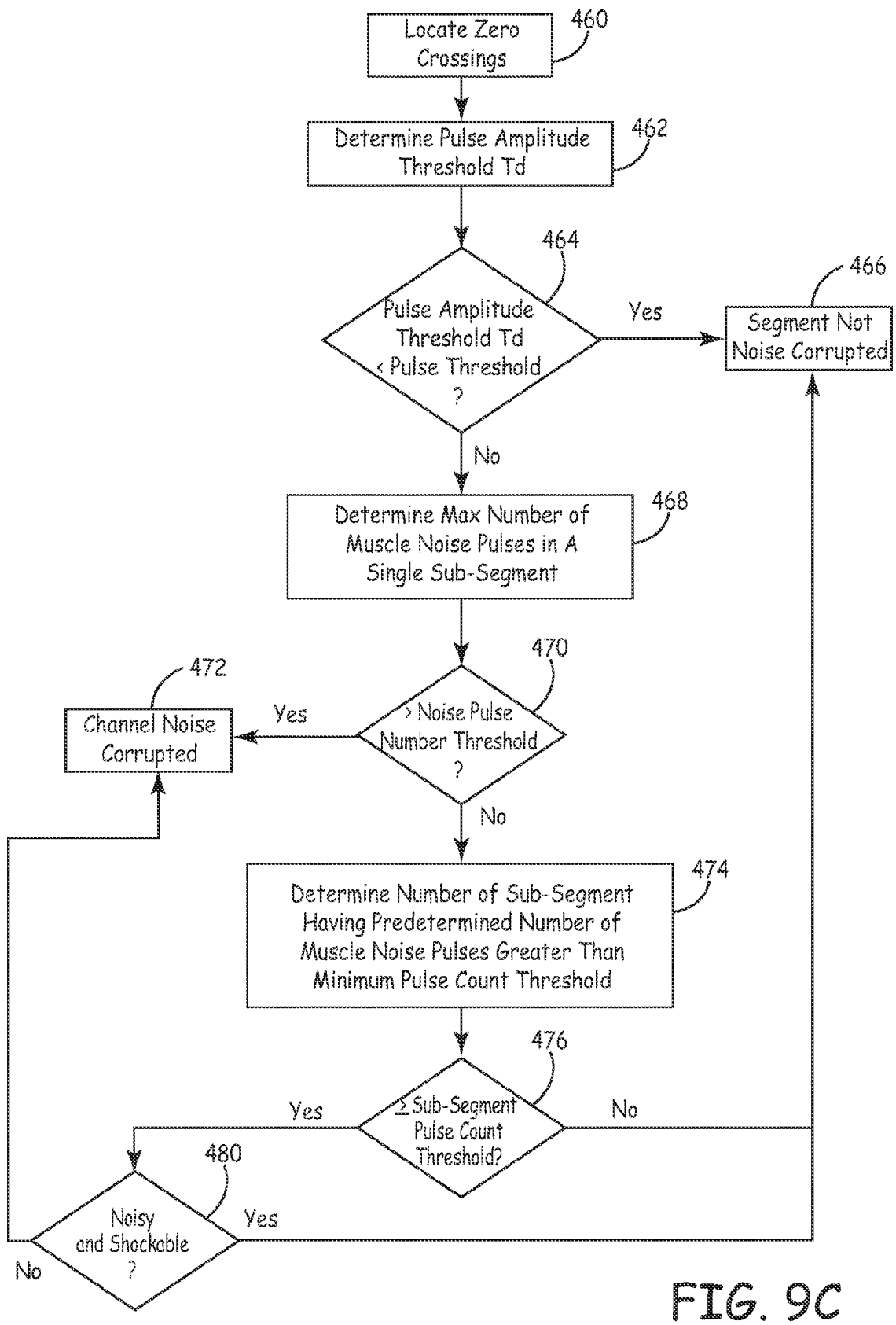
FIG. 9C is a flowchart of a method of determining whether a signal is corrupted by muscle noise according to an embodiment of the present invention.

FIG. 9C is a flowchart of a method of determining whether a signal is corrupted by muscle noise according to an embodiment of the present invention. Since muscle noise can be present during an episode of ventricular tachycardia, the width of the overall signal pulse waveform is determined in order to distinguish between signals that are determined likely to be purely noise related and signals that are both shockable events and determined to include noise. Therefore, as illustrated in FIG. 9C, according to an embodiment of the present invention, once muscle noise is determined to be present as a result of the muscle noise pulse count being satisfied, No in Block 470 and Yes in Block 476, a determination is made as to whether the signal is both noise corrupted and shockable, Block 480.

According to an embodiment of the present invention, the determination in Block 480 as to whether the signal is both noisy and shockable is made, for example, by dividing the rectified signal, having 768 data points, into four sub-segments and determining a maximum amplitude for each of the four sub-segments by determining whether a maximum amplitude for the sub-segment is less than a portion of the maximum amplitude for the entire rectified signal in the three second segment. For example, a determination is made for each sub-segment as to whether the maximum amplitude for the sub-segment is less than one fourth of the maximum amplitude for the entire rectified signal. If less than a portion of the maximum amplitude for the entire rectified signal in the three second segment, the maximum amplitude for the sub-segment is set equal to the maximum amplitude for the entire rectified signal.

A mean rectified amplitude for each of the sub-segments is determined by dividing the sum of the rectified amplitudes for the sub-segment by the number of samples in the sub-segment, i.e., 768÷4. Then the normalized mean rectified amplitude for each sub-segment is determined by dividing the mean rectified amplitude for each of the sub-segments by the peak amplitude for the sub-segment. The normalized mean rectified amplitude for the three second segment is then determined as the sum of the normalized mean rectified amplitudes for each sub-segment divided by the number of sub-segments, i.e., four.

Therefore, once muscle noise is suspected as a result of the determination of the muscle noise pulse count, the determination of Block 480 based on whether the normalized mean rectified amplitude for the three second segment is greater than a predetermined threshold for identifying signals that, despite being indicative of a likelihood of being associated with noise, nevertheless are associated with a shockable event. For example, according to an embodiment of the present invention, a determination is made as to whether the normalized mean rectified amplitude for the three second segment is greater than 18 microvolts. If the normalized mean rectified amplitude for the three second segment is less than or equal to the predetermined threshold, the channel is likely corrupted by muscle noise and not shockable, No in Block 480, and is therefore identified as being corrupted by noise, Block 472. If the normalized mean rectified amplitude for the three second segment is greater than the predetermined threshold, the channel is determined to be likely corrupted by muscle noise and shockable, Yes in Block 480, and is therefore identified as not to be likely corrupted by muscle noise, Block 478.

Returning to FIG. 7C, when the signal is determined to be not likely corrupted by muscle noise, a determination is made as to whether the mean frequency of the signal associated with the channel is less than a predetermined mean frequency threshold, Block 388, such as 11 Hz for example. The mean frequency of the signal during the 3 second segment for each channel ECG1 and ECG2 is generated, for example, by calculating the ratio of the mean absolute amplitude of the first derivative of the 3 second segment to the mean absolute amplitude of the 3 second segment, multiplied by a constant scaling factor. If the mean frequency is determined to be greater than or equal to the predetermined mean frequency threshold, No in Block 388, the three second segment for that channel is identified as being likely corrupted with noise, Block 386. If the mean frequency is determined to be less than the predetermined mean frequency threshold, Yes in Block 388, the three second segment for that channel is identified as being not noise corrupted, Block 390.

According to an embodiment of the present invention, since the mean spectral frequency tends to be low for true ventricular fibrillation events, moderate for organized rhythms such as sinus rhythm and supraventricular tachycardia, for example, and high during asystole and noise, the determination in Block 388 includes determining whether the mean frequency is less than a predetermined upper mean frequency threshold, such as 11 Hz (i.e., mean period T of approximately 91 milliseconds) for example, and whether the mean frequency is less than a predetermined lower mean frequency, such as 3 Hz for example. If the mean frequency is below a second, lower threshold, such as 3 Hz, for example, the signal is also rejected as noise and no further noise tests are initiated. This comparison of the mean frequency to a second lower threshold is intended to identify instances of oversensing, resulting in appropriate transition to the concerned state. If the mean frequency of the signal is less than 3 Hz, it is generally not possible for the heart rate to be greater than 180 beats per minute. In practice, it may be advantageous to set the lower frequency threshold equal to the programmed VT/VF detection rate, which is typically approximately 3 Hz.

Therefore, in the determination of Block 388, if the mean frequency is determined to be either greater than or equal to the predetermined upper mean frequency threshold or less than the lower threshold, the three second segment for that channel is identified as being likely corrupted with noise, Block 386. If the mean frequency is determined to be both less than the predetermined upper mean frequency threshold and greater than the lower threshold, the three second segment for that channel is identified as not being noise corrupted, Block 390.

Returning to FIG. 7B, once the determination as to whether the channels ECG1 and ECG2 are corrupted by noise is made, Block 342, a determination is made as to whether both channels are determined to be noise corrupted, Block 344. If the signal associated with both channels ECG1 and ECG2 is determined to likely be corrupted by noise, both channels are classified as being not shockable, Block 347, and therefore a buffer for each channel ECG1 and ECG2 containing the last three classifications of the channel is updated accordingly. If both channels ECG1 and ECG2 are not determined to be likely corrupted by noise, No in Block 344, the device distinguishes between either one of the channels being not corrupted by noise or both channels being not corrupted by noise by determining whether noise was determined to be likely in only one of the two channels ECG1 and ECG2, Block 346.

If noise was likely in only one of the two channels, a determination is made whether the signal for the channel not corrupted by noise, i.e., the clean channel, is more likely associated with a VT event or with a VF event by determining, for example, whether the signal for that channel includes R-R intervals that are regular and the channel can be therefore classified as being relatively stable, Block 348. If the R-R intervals are determined not to be relatively stable, NO in Block 348, the signal for that channel is identified as likely being associated with VF, which is then verified by determining whether the signal is in a VF shock zone, Block 350, described below. If R-R intervals for that channel are determined to be stable, YES in Block 348, the signal is identified as likely being associated with VT, which is then verified by determining whether the signal is in a VT shock zone, Block 352, described below.

If noise was not likely for both of the channels, No in Block 346, i.e., both channels are determined to be clean channels, a determination is made whether the signal for both channels is more likely associated with a VT event or with a VF event by determining whether the signal for both channels includes R-R intervals that are regular and can be therefore classified as being relatively stable, Block 356. If the R-R intervals are determined not to be relatively stable, NO in Block 356, the signal for both channels is identified as likely being associated with VF, which is then verified by determining whether the signal for each channel is in a VF shock zone, Block 360, described below. If R-R intervals for both channels are determined to be stable, YES in Block 356, the signal is identified as likely being associated with VT, which is then verified by determining, based on both channels, whether the signal is in a VT shock zone, Block 352.

Figure 7D:
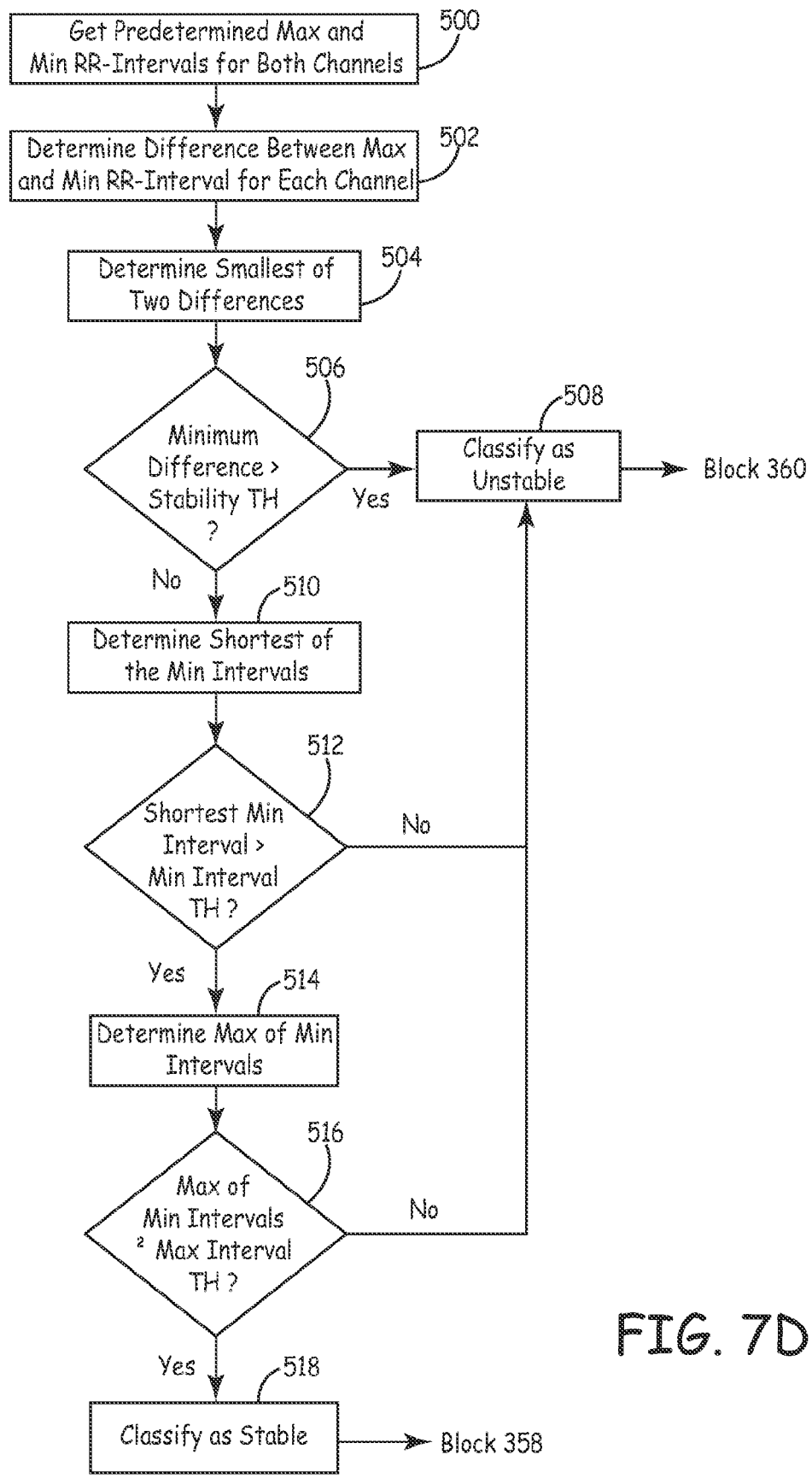

As illustrated in FIG. 7D, according to an embodiment of the present invention, in order to determine whether the signal for both channels includes R-R intervals that are regular and the channels can be therefore classified as being relatively stable, Block 356, predetermined maximum and minimum intervals for each channel ECG1 and ECG2 are identified, Block 500, from the updated buffer of 12 RR-intervals, Block 342. According to one embodiment of the present invention, the largest RR-interval and the sixth largest RR-interval of the twelve RR-intervals are utilized as the maximum interval and the minimum interval, respectively.

The difference between the maximum RR-interval and the minimum RR-interval of the 12 RR-intervals is calculated for each channel ECG1 and ECG2, Block 502, to generate a first interval difference associated with the first channel ECG1 and a second interval difference associated with the second channel ECG2. The smallest of the first interval difference and the second interval difference is then identified, Block 504, and a determination is made as to whether the minimum of the first interval difference and the second interval difference is greater than a predetermined stability threshold, Block 506, such as 110 milliseconds, for example.

If the minimum of the first interval difference and the second interval difference is greater than the stability threshold, the event is classified as an unstable event, Block 508, and a determination is made for each channel as to whether the signal associated with the channel is within a predetermined VF shock zone, Blocks 360 and 362 of FIG. 7B, described below. If the minimum of the first interval difference and the second interval difference is less than or equal to the stability threshold, No in Block 506, the device determines which one of the minimum RR-interval associated with the first channel ECG1 and the minimum RR-interval associated with the second channel ECG2 is shortest, Block 510, and determines whether the shortest minimum interval is greater than a minimum interval threshold, Block 512, such as 200 milliseconds, for example.

If the shortest of the two minimum intervals is less than or equal to the minimum interval threshold, the event is classified as an unstable event, Block 508, and a determination is made for each channel as to whether the signal associated with the channel is within a predetermined VF shock zone, Blocks 360 and 362 of FIG. 7B, described below. If the shortest of the two minimum intervals is greater than the minimum interval threshold, the device determines which one of the minimum RR-interval associated with the first channel ECG1 and the minimum RR-interval associated with the second channel ECG2 is the greatest, Block 514, and determines whether the maximum of the two minimum intervals is less than or equal to a maximum interval threshold, Block 516, such as 333 milliseconds for example. If the maximum of the two minimum intervals is greater than the maximum interval threshold, the event is classified as an unstable event, Block 508, and a determination is made for each channel as to whether the signal associated with the channel is within a predetermined VF shock zone, Blocks 360 and 362 of FIG. 7B, described below. If the maximum of the two minimum intervals is less than or equal to the maximum interval threshold, the event is classified as a stable event, Block 518, and a determination is made, based on both channels ECG1 and ECG2, as to whether the signal is within a predetermined VT shock zone, Block 358, described below.

Figure 7E:
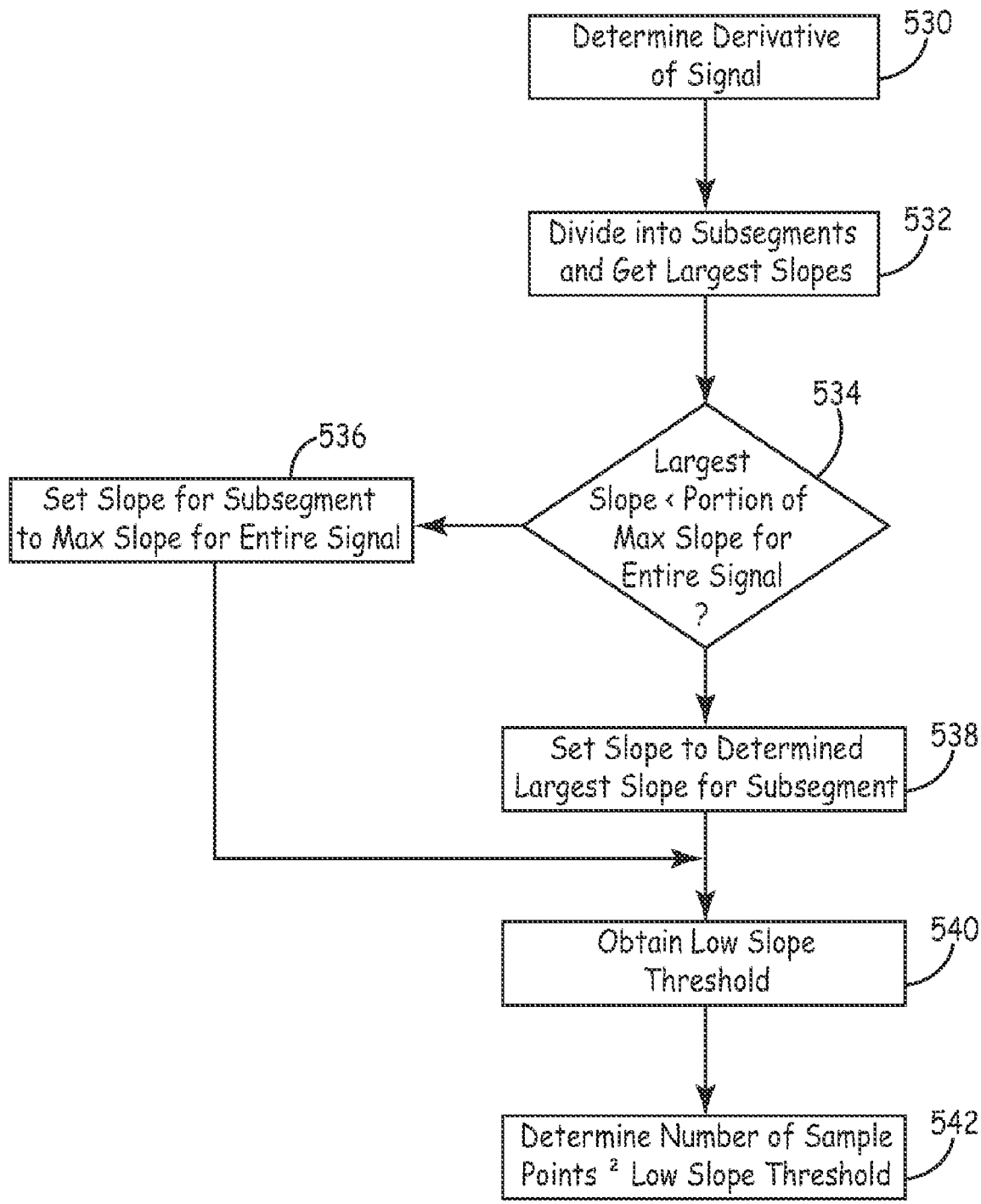

Returning to FIG. 7B, according to an embodiment of the present invention, during the determination of whether the signal associated with each of the channels ECG1 and ECG2 is within the VF shock zone, Blocks 360 and 362, the VF shock zone is defined based upon a low slope content metric and a spectral width metric for each of the two channels ECG1 and ECG2. The low slope content metric is calculated as the ratio of the number of data points with low slope to the total number of samples in the 3-second segment. For example, according to an embodiment of the present invention, the difference between successive ECG samples is determined as an approximation of the first derivative (i.e, the slope) of the ECG signal. In particular, as illustrated in FIG. 7E, the raw signal for each channel is applied to a first order derivative filter to obtain a derivative signal for the three-second segment, Block 530. The derivative signal is then rectified, divided into four equal sub-segments, and the largest absolute slope is estimated for each of the four sub-segments, Block 532.

A determination is made as to whether the largest absolute slopes are less than a portion of the overall largest absolute slope for the whole three-second segment, Block 534, such as one-fifth of the overall absolute slope, for example. If the largest absolute slope is less than the portion of the overall slope, then the slope value for that sub-segment is set equal to the overall largest absolute slope, Block 536. If the largest absolute slope is not less than the portion of the overall slope, then the slope value for that sub-segment is set equal to the determined largest absolute slope for the sub-segment, Block 538.

Once the slope value for each of the sub-segments has been determined and updated by being set equal to the largest slope for the three second segment, if necessary, the average of the four slopes is calculated and divided by a predetermined factor, such as 16 for example, to obtain a low slope threshold, Block 540. The low slope content is then obtained by determining the number of sample points in the three-second segment having an absolute slope less than or equal to the low slope threshold, Block 542.

According to an embodiment of the present invention, if, during the determination of the low slope threshold in Block 540, the low slope threshold is a fraction, rather than a whole number, a correction is made to the low slope content to add a corresponding fraction of the samples. For example, if the threshold is determined to be 4.5, then the low slope content is the number of sample points having an absolute slope less than or equal to 4 plus one half of the number of sample points with slope equal to 5.

The spectral width metric, which corresponds to an estimate of the spectral width of the signal for the three-second segment associated with each channel ECG1 and ECG2, is defined, for example, as the difference between the mean frequency and the fundamental frequency of the signal. According to an embodiment of the present invention, the spectral width metric is calculated by determining the difference between the most recent estimate of the RR-cycle length and the mean spectral period of the signal for that channel. As is known in the art, the mean spectral period is the inverse of the mean spectral frequency.

It is understood that R-R cycle length utilized in the concerned state and armed state can be different than that used in the not concerned state. For example, according to an embodiment of the present invention, the $9^{th}$ longest R-R interval is utilized in the not concerned state and the mean of the $7^{th}$ to the $10^{th}$ R-R interval is utilized in the concerned state and the armed state.

Figure 10:
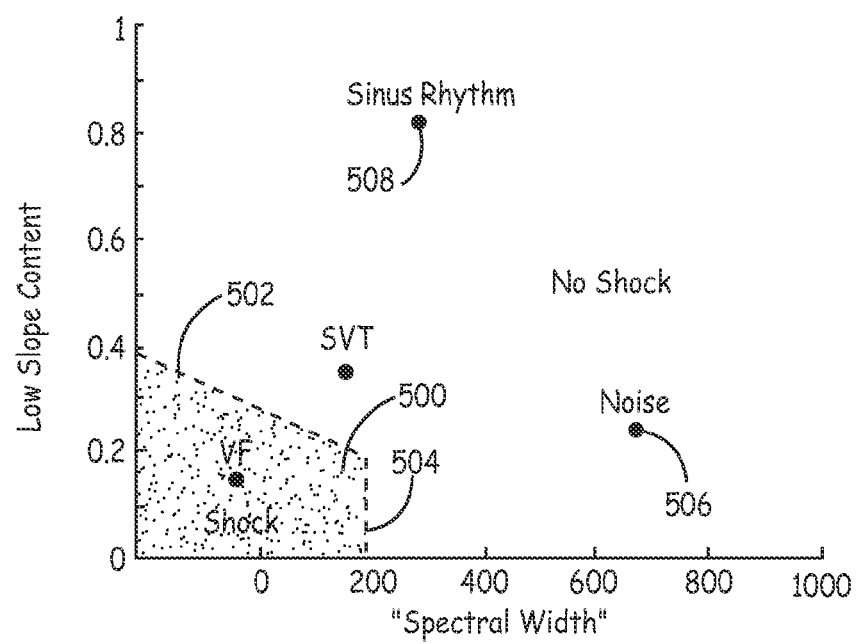
FIG. 10 is a graphical representation of a VF shock zone according to an embodiment of the present invention.

FIG. 10 is a graphical representation of a VF shock zone according to an embodiment of the present invention. As illustrated in FIG. 10, a VF shock zone 500 is defined for each channel ECG1 and ECG2 based on the relationship between the calculated low slope content and the spectral width associated with the channel. For example, the shock zone is defined by a first boundary 502 associated with the low slope content set for by the equation:

Low slope content=−0.0013×spectral width+0.415      Equation 1 and a second boundary 504 associated with the spectral width set forth by the equation:

spectral width=200      Equation 2

As can be seen in FIG. 10, since noise 506 tends to have a relatively higher spectral width, and normal sinus rhythm 508 tends to have a relatively higher low slope content relative to VF, both noise 506 and normal sinus rhythm 508 would be located outside the VF shock zone 500.

A determination is made for each channel ECG1 and ECG2 as to whether the low slope content for that channel is less than both the first boundary 502 and the spectral width is less than the second boundary 504, i.e., the low slope content is less than −0.0013×spectral width+0.415, and the spectral width is less than 200. For example, once the event is determined to be associated with VF, i.e., the intervals for both channels are determined to be irregular, No in Block 356, a determination is made that channel ECG1 is in the VF shock zone, Yes in Block 360, if, for channel ECG1, both the low slope content is less than the first boundary 502 and the spectral width is less than the second boundary 504. The three second segment for that channel ECG1 is then determined to be shockable, Block 363 and the associated buffer for that channel is updated accordingly. If either the low slope content for the channel is not less than the first boundary 502 or the spectral width is not less than the second boundary, the channel ECG1 is determined not to be in the VF shock zone, No in Block 360, the three second segment for that channel ECG1 is then determined to be not shockable, Block 365, and the associated buffer is updated accordingly.

Similarly, a determination is made that channel ECG2 is in the VF shock zone, Yes in Block 362, if, for channel ECG2, both the low slope content is less than the first boundary 502 and the spectral width is less than the second boundary 504. The three second segment for that channel ECG2 is then determined to be shockable, Block 369 and the associated buffer for that channel is updated accordingly. If either the low slope content for the channel is not less than the first boundary 502 or the spectral width is not less than the second boundary, the channel ECG2 is determined not to be in the VF shock zone, No in Block 362, the three second segment for that channel ECG2 is then determined to be not shockable, Block 367, and the associated buffer is updated accordingly.

Figure 11A:
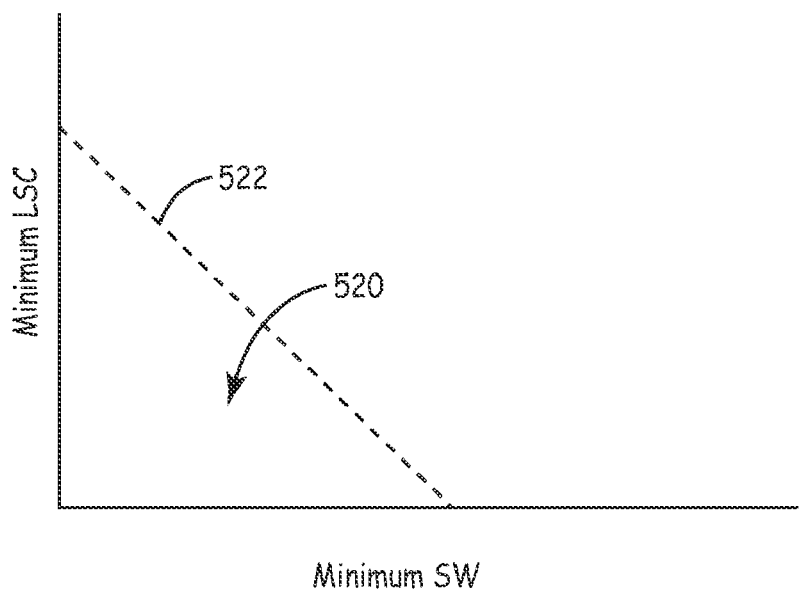
FIGS. 11A and 11B are graphical representations of the determination of whether an event is within a shock zone according to an embodiment of the present invention.
Figure 11B:
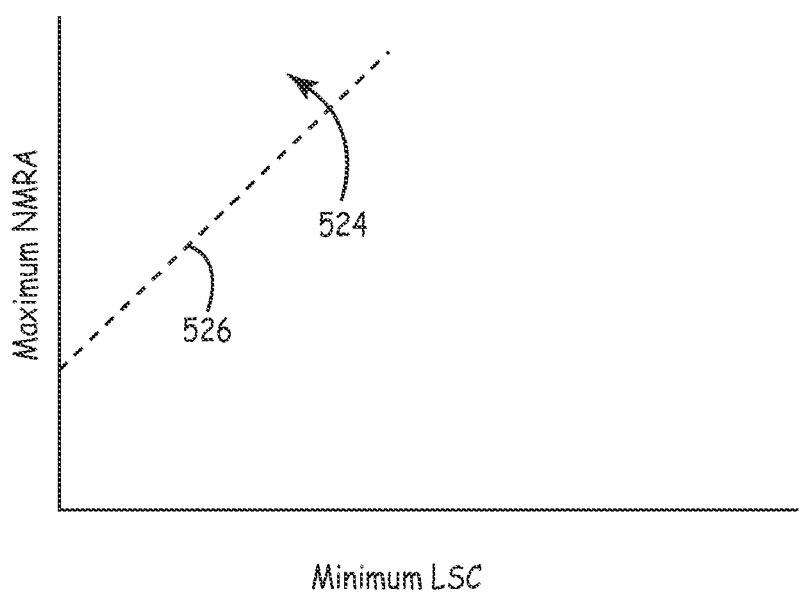

FIGS. 11A and 11B are graphical representations of the determination of whether an event is within a shock zone according to an embodiment of the present invention. During the determination of whether the event is within the VT shock zone, Block 358 of FIG. 7B, the low slope content and the spectral width is determined for each channel ECG1 and ECG2, as described above in reference to determining the VF shock zone. A determination is made as to which channel of the two signal channels ECG1 and ECG2 contains the minimum low slope content and which channel of the two signal channels ECG1 and ECG2 contains the minimum spectral width. A first VT shock zone 520 is defined based on the relationship between the low slope content associated with the channel determined to have the minimum low slope content and the spectral width associated with the channel determined to have the minimum spectral width. For example, according to an embodiment of the present invention, the first VT shock zone 520 is defined by a boundary 522 associated with the minimum low slope content and the minimum spectral width set forth by the equation:

$$LSC = -0.004 \times SW + 0.93 \qquad \text{Equation 3}$$

A second VT shock zone 524 is defined based on the relationship between the low slope content associated with the channel determined to have the minimum low slope content and the normalized mean rectified amplitude associated with the channel determined to have the maximum normalized mean rectified amplitude. The normalized mean rectified amplitudes for the two channels ECG1 and ECG2 utilized during the VT shock zone test is the same as described above in reference to the noise determination of Block 343. For example, according to an embodiment of the present invention, the second VT shock zone 524 is defined by a second boundary 526 associated with the relationship between the minimum low slope count and the maximum normalized mean rectified amplitude set forth by the equation:

$$NMRA = 68 \times LSC + 8.16 \qquad \text{Equation 4}$$

If both the minimum low slope count is less than the first boundary 522, i.e., −0.004×minimum spectral width+0.93, and the maximum normalized mean rectified amplitude is greater than the second boundary 526, i.e., 68× minimum low slope count+8.16, the event is determined to be in the VT shock zone, YES in Block 358, and both channels ECG1 and ECG2 are determined to be shockable, Block 357, and the associated buffers are updated accordingly. If either the minimum low slope count is not less than the first boundary 522 or the maximum normalized mean rectified amplitude is not greater than the second boundary 526, the event is determined to be outside the VT shock zone, NO in Block 358, and both channels ECG1 and ECG2 are determined to be not shockable, Block 359.

As described, during both the VF shock zone test, Blocks 360 and 362, and the VT shock zone test, Block 358, the test results for each channel ECG1 and ECG2 as being classified as shockable or not shockable are stored in a rolling buffer containing the most recent eight such designations, for example, for each of the two channels ECG1 and ECG2 that is utilized in the determination of Block 356, as described below.

If only one of the two channels ECG1 and ECG2 is determined to be corrupted by noise, Yes in Block 346, a determination is made whether the signal for the channel not corrupted by noise, i.e., the "clean channel", is more likely associated with a VT event or with a VF event by determining whether the signal for the clean channel includes R-R intervals that are regular and can be therefore classified as being relatively stable, Block 348. If the R-R intervals are determined not to be relatively stable, NO in Block 348, the signal for the clean channel is identified as likely being associated with VF, which is then verified by determining whether the signal for the clean channel is in a VF shock zone, Block 350, described below. If R-R intervals for the clean channel are determined to be stable, YES in Block 348, the signal is identified as likely being associated with VT, which is then verified by determining whether the signal for the clean channel is in a VT shock zone, Block 352.

Figure 7F:
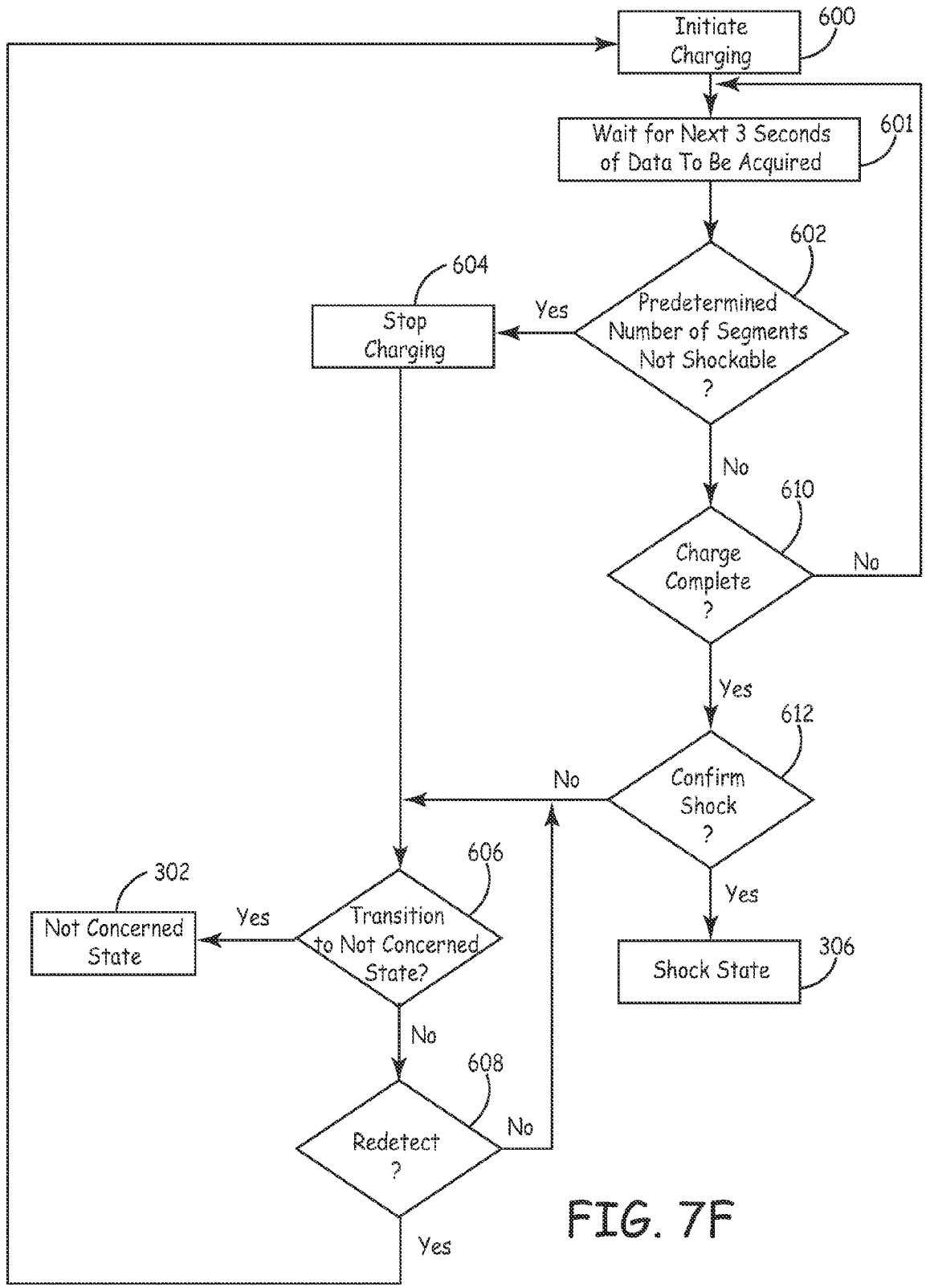

According to an embodiment of the present invention, in order to determine whether the signal for the clean channel includes R-R intervals that are regular and the clean channel can be therefore classified as being either relatively stable, Yes in Block 348, or relatively unstable, No in Block 348, the device discriminates VT events from VF events in Block 348 by determining whether the relative level of variation in the RR-intervals associated with the clean channel is regular. For example, as illustrated in FIG. 7H, predetermined maximum and minimum intervals for the clean channel are identified, Block 700, from the updated buffer of 12 RR-intervals, Block 342 of FIG. 7B. According to an embodiment of the present invention, the largest RR-interval and the sixth largest RR-interval of the twelve RR-intervals are utilized as the maximum interval and the minimum interval, respectively.

The difference between the maximum RR-interval and the minimum RR-interval of the 12 RR-intervals is calculated to generate an interval difference associated with the clean channel, 702. A determination is then made as to whether the interval difference is greater than a predetermined stability threshold, Block 704, such as 110 milliseconds, for example.

If the interval difference is greater than the stability threshold, the event is classified as an unstable event, Block 706, and therefore the clean channel is determined not to include regular intervals, No in Block 348, and a determination is made as to whether the signal associated with the clean channel is within a predetermined VF shock zone, Block 350 of FIG. 7B, described below. If the interval difference is less than or equal to the stability threshold, No in Block 704, the device determines whether the minimum RR interval is greater than a minimum interval threshold, Block 710, such as 200 milliseconds, for example.

If the minimum interval is less than or equal to the minimum interval threshold, No in Block 710, the event is classified as an unstable event, Block 706, and therefore the clean channel is determined not to include regular intervals, No in Block 348, and a determination is made as to whether the signal associated with the clean channel is within a predetermined VF shock zone, Block 350 of FIG. 7B, described below. If the minimum interval is greater than the minimum interval threshold, Yes in Block 710, the device determines whether the maximum interval is less than or equal to a maximum interval threshold, Block 712, such as 333 milliseconds for example. If the maximum interval is greater than the maximum interval threshold, the event is classified as an unstable event, Block 706, and therefore the clean channel is determined not to include regular intervals, No in Block 348, and a determination is made as to whether the signal associated with the clean channel is within a predetermined VF shock zone, Block 350 of FIG. 7B, described below. If the maximum interval is less than or equal to the maximum interval threshold, the event is classified as a stable event, Block 714, and therefore the clean channel is determined to include regular intervals, Yes in Block 348, and a determination is made as to whether the signal associated with the clean channel is within a predetermined VT shock zone, Block 352 of FIG. 7B, described below.

Returning to FIG. 7B, the determination of whether the clean channel is within the VF shock zone, Block 350, is made based upon a low slope content metric and a spectral width metric, similar to the VF shock zone determination described above in reference to Blocks 360 and 362, both of which are determined for the clean channel using the method described above. Once the low slope content metric and a spectral width metric are determined for the clean channel, the determination of whether the clean channel is in the VF shock zone is made using Equations 1 and 2, so that if either the low slope content for the clean channel is not less than the first boundary 502 or the spectral width is not less than the second boundary 504, the clean channel is determined not to be in the VF zone, No in Block 350 and both channels are classified as not shockable, Block 351, and the associated buffers are updated accordingly.

If the low slope content for the clean channel is less than the first boundary 502 and the spectral width is less than the second boundary 504, the clean channel is determined to be in the VF zone, Yes in Block 350. A determination is then made as to whether the channel determined to be corrupted by noise, i.e., the "noisy channel", is within the VF shock zone, Block 354. If either the low slope content for the noisy channel is not less than the first boundary 502 or the spectral width is not less than the second boundary 504, the noisy channel is determined not to be in the VF zone, No in Block 354, the clean channel is classified as shockable and the noisy channel is classified as not shockable, Block 355, and the associated buffers are updated accordingly.

If the low slope content for the noisy channel is less than the first boundary 502 and the spectral width is less than the second boundary 504, the noisy channel is determined to be in the VF zone, Yes in Block 354, both the clean channel and the noisy channel are classified as being shockable, Block 353, and the associated buffers are updated accordingly.

Similar to the VT shock zone determination described above in reference to Block 358, during the determination as to whether the clean channel is within the VT shock zone in Block 352, the low slope content and the spectral width is determined for the clean channel as described above in reference to determining the VF shock zone. The first VT shock zone 520 is defined based on the relationship between the low slope content and the spectral width associated with the clean channel according to Equation 3, for example, and the second VT shock zone 524 is defined based on the relationship between the low slope count and the normalized mean rectified amplitude associated with the clean channel. The normalized mean rectified amplitudes for the clean channel is the same as described above in reference to the noise detection tests of Block 344. For example, according to an embodiment of the present invention, the second VT shock zone 524 is defined by a second boundary 526 associated with the relationship between the low slope count and the normalized mean rectified amplitude of the clean channel using Equation 4.

If both the low slope count is less than the first boundary 522, i.e., −0.004×spectral width of clean channel+0.93, and the normalized mean rectified amplitude is greater than the second boundary 526, i.e., 68× low slope count of clean channel+8.16, the clean channel is determined to be in the VT shock zone, Yes in Block 352, both channels are classified as being shockable, Block 353, and the associated buffers are updated accordingly.

If either the low slope count is not less than the first boundary 522 or the maximum normalized mean rectified amplitude is not greater than the second boundary 526, the clean channel is determined to be outside the VT shock zone, No in Block 352, both channels are classified as being not shockable, Block Block 351, and the associated buffers are updated accordingly.

Once the classification of both of the channels ECG1 and ECG2 is made subsequent to the determination of whether the clean channel or channels is in the VT shock zone, Block 352 and 358, or the VF shock zone, Blocks 350 and Blocks 360 and 362 in combination, a determination is made as to whether the device should transition from the concerned state 304 to the armed state 306, Block 370. For example, according to an embodiment of the present invention, the transition from the concerned state 304 to the armed state 306 is confirmed if a predetermined number, such as two out of three for example, of three-second segments for both channels ECG1 and ECG2 have been classified as being shockable. If the predetermined number of three-second segments in both channels ECG1 and ECG2 have been classified as shockable, the device transitions from the concerned state 304 to the armed state 306, Yes in Block 370. If the predetermined number of three-second segments in both channels ECG1 and ECG2 have not been classified as shockable, the device does not transition from the concerned state 304 to the armed state 306, no in Block 370, and a determination as to whether to transition back to the not concerned state 302 is made, Block 372. The determination as to whether to transition from the concerned state 304 back to the not concerned state 302 is made, for example, by determining whether the heart rate estimate is less than a heart rate threshold level in both of the two channels ECG1 and ECG2. If it is determined that the device should not transition to the not concerned state 302, i.e., both of the two heart rate estimates are greater than the heart rate threshold, the process is repeated using the signal generated during a next three-second window, Block 341.

According to an embodiment of the present invention, the heart rate threshold level is set as 180 bpm, for example, and a single estimate of heart rate (that occurs every three seconds) in at least one of the two channels ECG1 and ECG2 that is less than the heart rate threshold level will suffice to cause the device to transition from the concerned state 304 to the not concerned state 302, Yes in Block 372.

When the device transitions from the concerned state 304 to the armed state 306, Yes in Block 370, processing continues to be triggered by a three-second time out as is utilized during the concerned state 304, described above. As illustrated in FIG. 7F, once the device transitions from the concerned state 302 to the armed state 306, charging of the capacitors is initiated, Block 600. During the charging of the capacitors, the classification of segments for each channel ECG1 and ECG2 as being either shockable or not shockable generated during the shock zone tests described above continues and once the next three seconds of data has been acquired, Block 601, a determination is made as whether the event continues to be a shockable event by determining whether a predetermined number of segments, such as the most recent two segments for example, have been classified in both of the two channels ECG1 and ECG2 as not shockable, Block 602. If the predetermined number of three second segments have been classified as not shockable, indicating that the event may possibly no longer be a shockable event, Yes in Block 602, the charging of the capacitors is stopped, Block 604, and a determination is made as to whether to terminate delivery of the shock therapy, i.e., transition to the not concerned state 302, Block 606.

According to an embodiment of the present invention, the device will transition from the armed state 306 to the not concerned state 302, Yes in Block 606, if certain termination requirements are met. For example, return to the not concerned state 302 occurs if, for both channels ECG1 and ECG2 simultaneously, less than two out of the last three three-second segments are classified as shockable, less than three out of the last eight three-second segments are classified as shockable, and the most recent three second segment is classified as not shockable. Another possible criteria for returning to the not concerned state 302 is the observation of 4 consecutive not shockable classifications in both channel ECG1 and ECG2 simultaneously.

In addition to the two criteria described above, at least one of the current heart rate estimates must be slower than the programmed rate threshold 403, and capacitor charging must not in progress. If each of these requirements are satisfied, Yes in Block 606, the device transitions from the armed state 306 to the not concerned state 302.

If one or more of these requirements are determined not to be satisfied, return to the not concerned state is not indicated, No in Block 606, and a determination is then made as whether the shockable rhythm is redetected, Block 608, by determining whether predetermined redetection requirements have been satisfied. For example, a determination is made as to whether a predetermined number of three-second segments in both of the two channels ECG1 and ECG2, such as two out of the most recent three for example, have been classified as being shockable. If the predetermined redetection requirements are not satisfied, No in Block 608, the determination of whether to terminate delivery of the therapy, Block 606, is repeated so that the processing switches between the determination of whether to terminate delivery of therapy, Block 606 and the determination as to whether the shockable event is redetected, Block 608, until either the event has terminated and the device transitions from the armed state 306 to the not concerned state 302 or the event is redetected. If the predetermined redetection requirements are met, Yes in Block 608, charging is re-initiated, Block 600, and the process is repeated.

If, during the charging of the capacitors, the predetermined number of three second segments have not been classified as not shockable, No in Block 602, a determination is made as to whether the charging of the capacitors is completed, Block 610. As long as the predetermined number of three second segments continue to be classified as shockable, No in Block 602, charging of the capacitors continues until charging is completed. Once the charging of the capacitors is completed, Yes in Block 610, a determination is made as to whether delivery of the therapy is still appropriate, Block 612, by determining whether predetermined therapy delivery confirmation requirements have been satisfied. For example, according to an embodiment of the present invention, the predetermined therapy delivery confirmation requirements include determining whether, for both channels ECG1 and ECG2, at least five out of the last eight three-second segments are classified as being shockable, and at least two of the last three three-second segments are classified as being shockable. In addition, a determination is made as to whether the most recent three-second segment has been classified as being shockable for at least one of the two channels ECG1 and ECG2.

If the predetermined therapy delivery requirements have not been satisfied, and therefore the delivery of the therapy is not confirmed, No in Block 612, the determination of whether to transition from the armed state 306 to the not concerned state 302, Block 606, is repeated. If the predetermined therapy delivery requirements are satisfied, and therefore the delivery of the therapy is confirmed, Yes in Block 612, the device transitions from the armed state 306 to the shock state 308.

Figure 12:
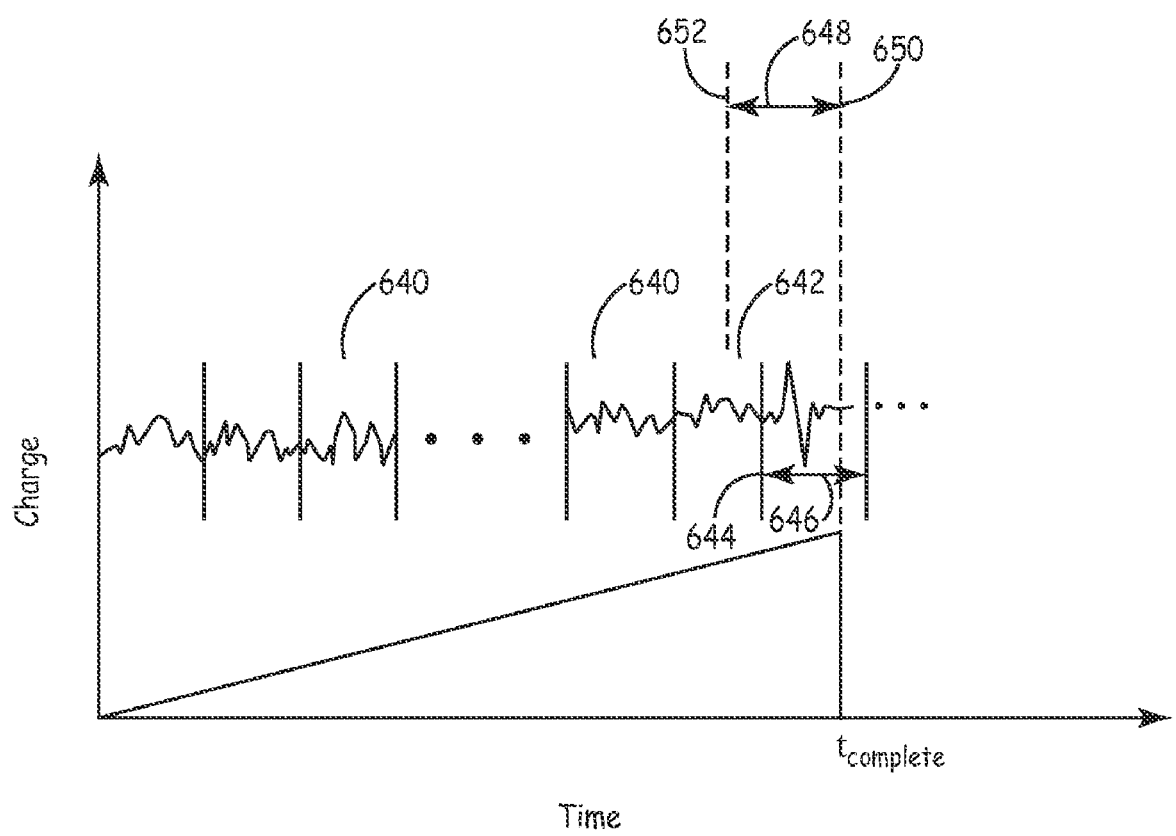
FIG. 12 is a graphical representation of charging of a medical device according to an embodiment of the present invention.

FIG. 12 is a graphical representation of charging of a medical device according to an embodiment of the present invention. During charging of the capacitors while the device is in the armed state, the classification of segments 640 for each channel ECG1 and ECG2 as being shockable or not shockable continues, as described above, until the charging of the capacitors is completed at time $t_{complete}$. As can be seen in FIG. 12, since a three second sensing window is utilized to classify the event as either shockable or not shockable, as described above, the final segment 642 of the segments 640 utilized during the classification typically has an endpoint 644 that occurs prior to when charging is completed, time $t_{complete}$. As a result, there is likely a window of time 646 less than the time period associated with the predetermined sensing window corresponding to segments 640 (i.e., three seconds, or example) that occurs just prior to the charging of the capacitors being completed, time $t_{complete}$.

If, as illustrated in FIG. 12, the cardiac event were to self-terminate during the window time 646 occurring between the last segment 642 utilized in the classification of the segments 640 and the completion of the charging of the capacitors at time $t_{complete}$, the morphology of the cardiac signal will therefore return to a normal rhythm, and therefore delivery of the shock therapy may no longer be necessary. However, since the completion of the determination of whether shock therapy should be delivered corresponds to the endpoint 644 of the final segment 642, such an occurrence of self-termination of the event occurring just prior to delivery of the shock therapy would typically not be recognized, and therefore the shock therapy may be delivered unnecessarily. Therefore, as illustrated in FIG. 7J, according to an embodiment of the present invention, in order to reduce the unnecessary delivery of shock therapy, an asynchronous look back is performed in which a determination is made as to whether the morphology of the signal during a three second window 648 occurring just prior to the charging of the capacitors being completed, time $t_{complete}$, is indicative of the cardiac event and therefore the delivery of the shock is confirmed, Block 613.

As illustrated in FIG. 12, the three second window 648 utilized during the asynchronous look back in the confirmation of the necessity for delivery of the shock in Block 613 includes an endpoint 650 corresponding to the charging of the capacitors being completed, time $t_{complete}$, and a start point 652 prior to the charging of the capacitors being completed, time $t_{complete}$, such as three seconds for example. The classification of the segment 648 as either "shockable" or "not shockable" during this look back period 648 is performed using the classification techniques described above.

Returning to FIG. 7J, according to an embodiment of the present invention, once the charging of the capacitors is determined to have been completed, Yes in Block 610, and the delivery of the shock is confirmed, Yes in Block 612, a determination is made as to whether delivery of the shock therapy is confirmed for each of channels ECG1 and ECG2 during the asynchronous look back segment 648 prior to the charging of the capacitors being completed, time $t_{complete}$. If the look back segment 648 is determined to be shockable in one or both of the channels ECG1 and ECG2, delivery of the shock is confirmed, Yes in Block 613, and the device transitions to the shock state 306. If the look back segment 648 is determined to be not shockable in both of the channels ECG1 and ECG2, delivery of the shock is not confirmed, No in Block 613, and the determination is made as to whether to terminate delivery of the shock, Block 606, using the process described above. The remaining steps associated with processing while in the armed state illustrated in FIG. 7J correspond to those processes described above in reference to FIG. 7F, and therefore description thereof is omitted merely for the sake of brevity.

Figure 7G:
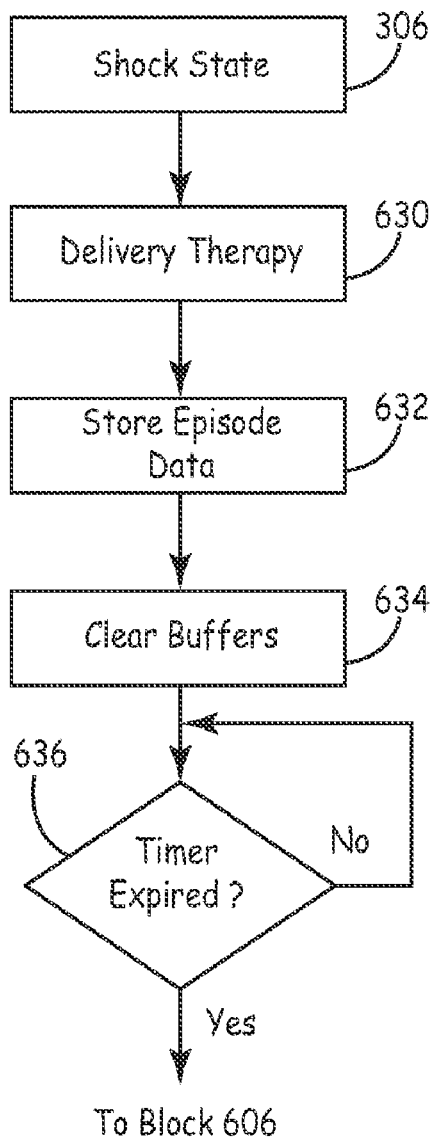
Figure 7H:
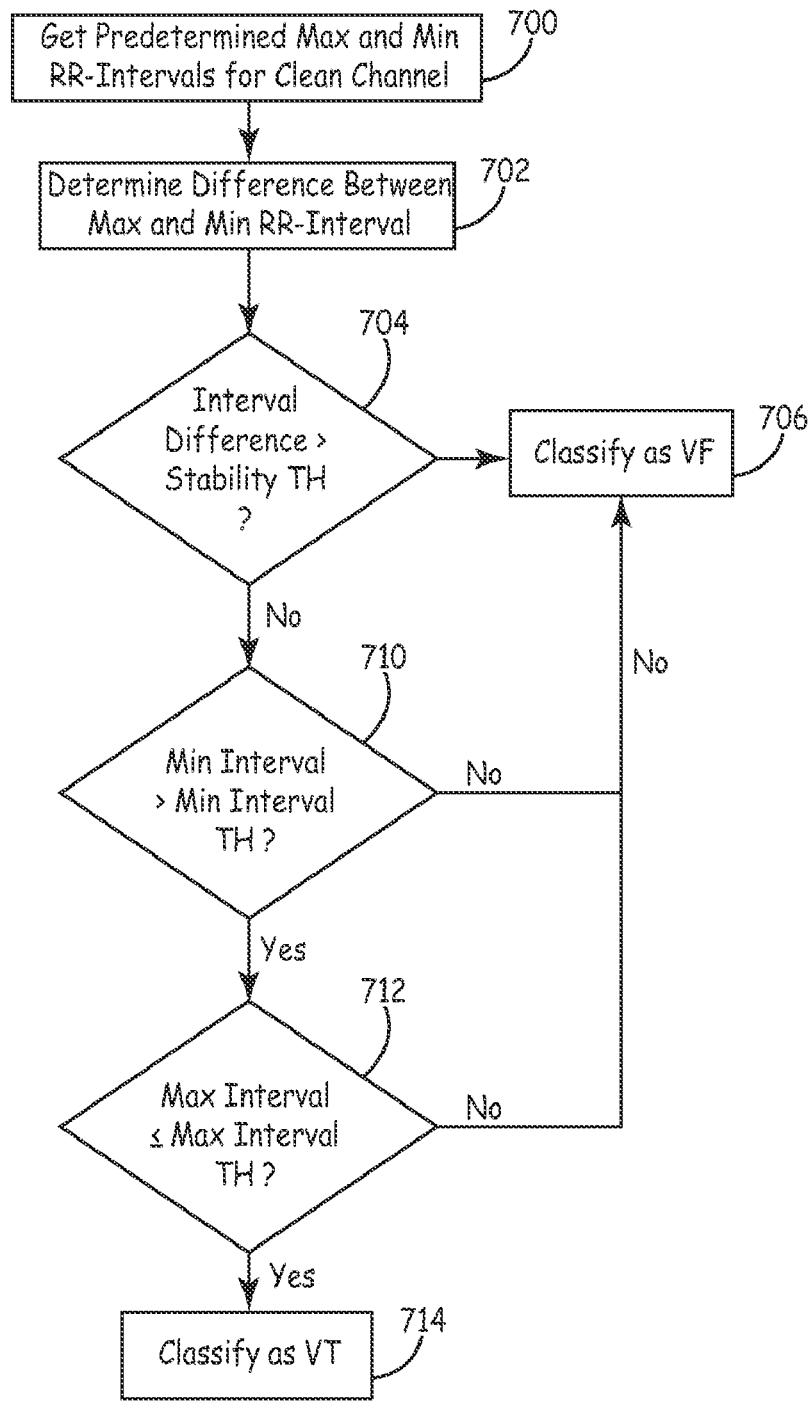

As illustrated in FIG. 7G, once the device transitions from the armed state 306 to the shock state 308, the therapy is delivered upon observation of the first sensed R-wave, Block 630, the episode data is stored, Block 632, and the buffers for storing the eight three second segments are cleared, Block 634. Once a post shock timer, such as three seconds for example, has expired, Yes in Block 636, the device transitions from the shock state 308 to Block 606 of the armed state 306. Since, as described above, classification of at least three subsequent three-second segments is required before the termination decision can be made in Block 606 subsequent to the delivery of therapy in the shock state 308, a determination based on the termination requirements cannot be initiated until at least twelve seconds after the initial shock therapy was delivered. The termination and redetection requirements are then reviewed until one of the two requirements are satisfied, i.e., the event is determined to have terminated, Yes in Block 606, or the event is redetected, Yes in Block 608. If the redetection requirements are satisfied, the charging of the capacitors is again initiated, Block 600, and processing in the armed state 306 continues as described above until all available therapies have been exhausted.

Figure 7I:
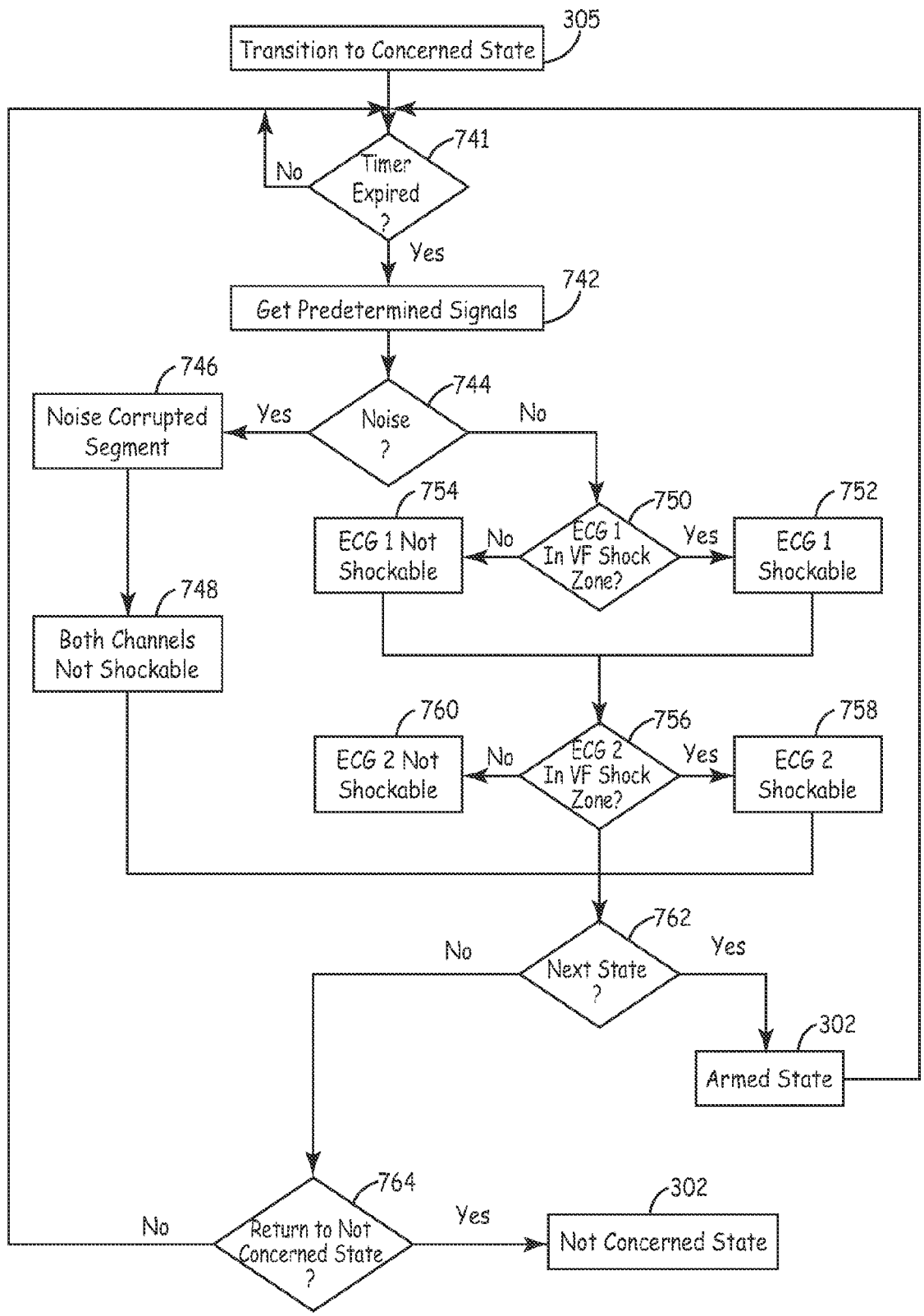
Figure 7J:
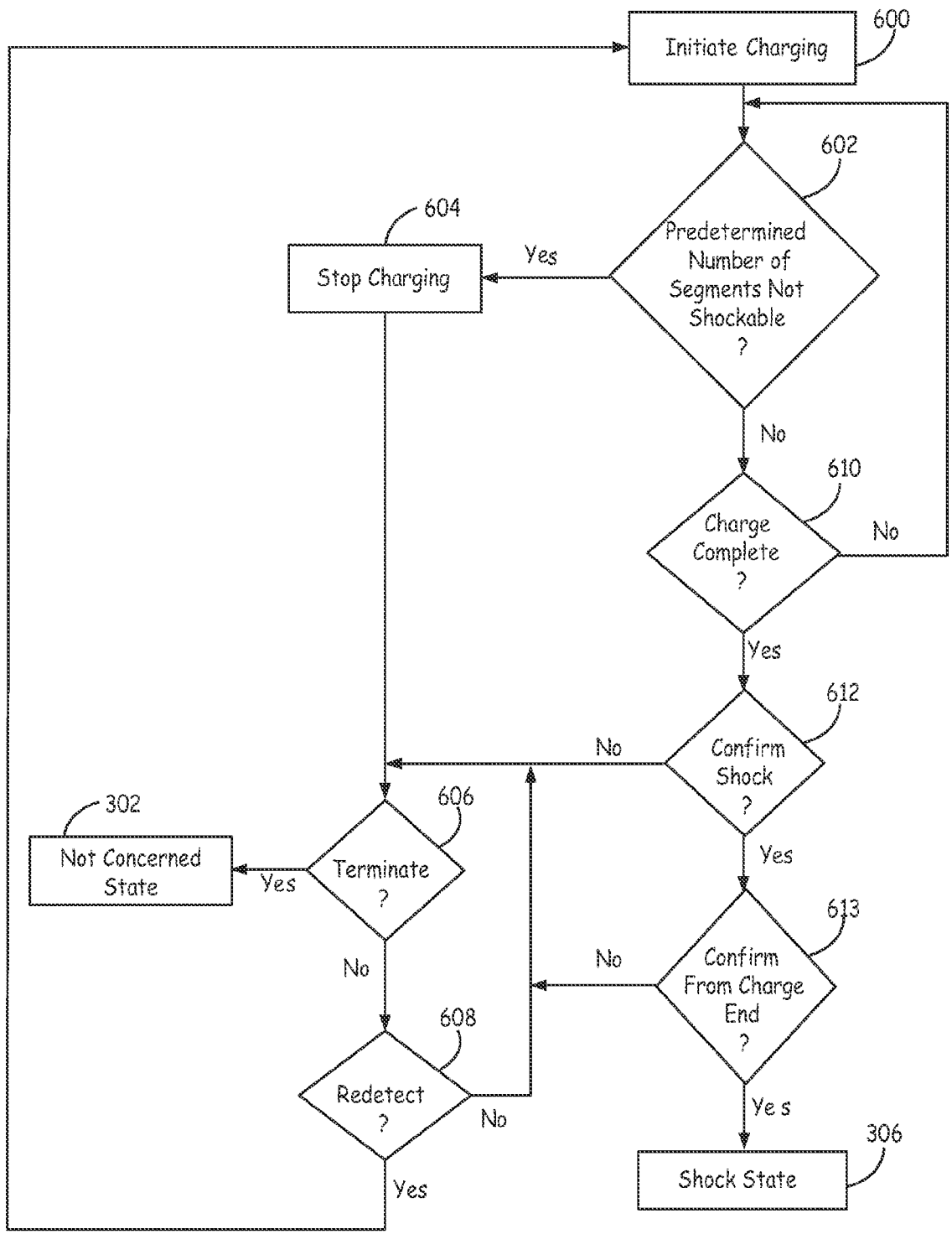

It will be apparent from the foregoing that while particular embodiments of the invention have been illustrated and described, various modifications can be made without departing from the spirit and scope of the invention. Accordingly, it is not intended that the invention be limited, except as by the appended claims. For example, as illustrated in FIG. 7I, during the noise determination of Block 744, the determination is made for each channel ECG1 and ECG2 as to whether the channel is corrupted by noise as described above. However, according to an embodiment of the present invention, once noise is determined to be present in either channel, No in Blocks 380, 382 or 388, Yes in Block 384 of FIG. 7C, both channels are classified as being not shockable, Block 748.

If noise is not present in either channel ECG1 and ECG2, No in Block 744, a determination is made as for each channel ECG1 and ECG2 as to whether the channel is in a VF shock zone. For example, according to an embodiment of the present invention, a determination is made that channel ECG1 is in the VF shock zone, Yes in Block 748, if, for channel ECG1, both the low slope content is less than the first boundary 502 and the spectral width is less than the second boundary 504, as described above. The three second segment for that channel ECG1 is then determined to be shockable, Block 750 and the associated buffer for that channel is updated accordingly. If either the low slope content for the channel is not less than the first boundary 502 or the spectral width is not less than the second boundary, the channel ECG1 is determined not to be in the VF shock zone, No in Block 748, the three second segment for that channel ECG1 is then determined to be not shockable, Block 752, and the associated buffer is updated accordingly.

Similarly, a determination is made that channel ECG2 is in the VF shock zone, Yes in Block 754, if, for channel ECG2, both the low slope content is less than the first boundary 502 and the spectral width is less than the second boundary 504, as described above. The three second segment for that channel ECG2 is then determined to be shockable, Block 756 and the associated buffer for that channel is updated accordingly. If either the low slope content for the channel is not less than the first boundary 502 or the spectral width is not less than the second boundary, the channel ECG2 is determined not to be in the VF shock zone, No in Block 754, the three second segment for that channel ECG2 is then determined to be not shockable, Block 758, and the associated buffer is updated accordingly.

Once the classification of both of the channels ECG1 and ECG2 as being either shockable, Block 752 and 758, or not shockable, Blocks 748, 754 and 760, a determination is made as to whether the device should transition from the concerned state 304 to the armed state 306, Block 762. The determination of whether the device should transition from the concerned state 304 to the armed state 306 in Block 762, in addition to the subsequent determination of whether to transition from the concerned state 304 to the not concerned state 302 in Block 764 are similar to the determination of whether the device should transition from the concerned state 304 to the armed state 306 in Block 370, and to the determination of whether to transition from the concerned state 304 to the not concerned state 302 in Block 372 in FIG. 7B described above, and therefore will not be repeated for the sake of brevity.

Some of the techniques described above may be embodied as a computer-readable medium comprising instructions for a programmable processor such as microprocessor 142, pacer/device timing circuit 178 or control circuit 144 shown in FIG. 3. The programmable processor may include one or more individual processors, which may act independently or in concert. A "computer-readable medium" includes but is not limited to any type of computer memory such as floppy disks, conventional hard disks, CR-ROMS, Flash ROMS, nonvolatile ROMS, RAM and a magnetic or optical storage medium. The medium may include instructions for causing a processor to perform any of the features described above for initiating a session of the escape rate variation according to the present invention.

While a particular embodiment of the present invention has been shown and described, modifications may be made. It is therefore intended in the appended claims to cover all such changes and modifications, which fall within the true spirit and scope of the invention.

We claim:

1. A medical device for detecting a cardiac event and delivering a corresponding therapy, the device comprising:
a plurality of electrodes configured to detect cardiac signals along a first sensing vector and a second sensing vector;
an energy storage device; and
a control unit configured to:
identify the cardiac event;
initiate charging of the energy storage device; then
sense a cardiac signal on each of the first sensing vector and the second sensing vector; then
deliver a charge from the energy storage device upon a completion of charging of the energy storage device if the cardiac signal sensed by at least one of the first sensing vector and the second sensing vector during a predetermined look back sensing window having a start time and an ending time is indicative of the cardiac event, the ending time of the predetermined look back sensing window being based on and no later than a time of completion of the charging of the energy storage device.

2. The device of claim 1, wherein the plurality of electrodes are positioned non-transvenously.

3. The device of claim 1, wherein the control unit is configured to deliver the charge upon completion of the charging of the energy storage device if a morphology of the cardiac signal sensed by at least one of the first sensing vector and the second sensing vector during the look back sensing window is indicative of the cardiac event.

4. The device of claim 3, wherein the control unit is configured to not deliver the charge upon completion of the charging of the energy storage device if the morphology of the cardiac signal sensed both of the first sensing vector and the second sensing vector during the look back sensing window is not indicative of the cardiac event.

5. The device of claim 1, wherein the starting time of the predetermined look back sensing window and the ending time of the predeteimined look back sensing window defines a duration between approximately 0.5 and 10 seconds.

6. The device of claim 3, wherein the control unit is configured to deliver the charge from the energy storage device upon a completion of charging further based, at least in part, on if the cardiac signal sensed by at least one of the first sensing vector and the second sensing vector during a sensing window being different than the first predetermined look back sensing window and having a starting time and a ending time is indicative of the cardiac event, the ending time of the sensing window not being concurrent with the completion of the charging of the energy storage device.

7. The device of claim 1 wherein the starting time is based on the time of completion of the charging of the energy storage device.

8. The device of claim 1 wherein the predetermined look back sensing window has a fixed duration.

9. The device of claim 1 wherein the ending time of the predetermined look back sensing window is concurrent with the completion of charging.

10. A medical device for detecting a cardiac event and delivering a corresponding therapy, the device comprising:
   means for detecting cardiac signals from a plurality of electrodes forming a first sensing vector and a second sensing vector;
   an energy storage device;
   means for identifying the cardiac event;
   means for initiating charging of the energy storage device in response to identifying the cardiac event;
   means for sensing a cardiac signal on each of the first sensing vector and the second sensing vector after initiating charging of the energy storage device;
   means for delivering a charge from the energy storage device upon a completion of charging of the energy storage device if the cardiac signal sensed by at least one of the first sensing vector and the second sensing vector during a predetermined look back sensing window having a start time and a ending time is indicative of the cardiac event, the ending time of the predetermined look back sensing window being based on and no later than a time of completion of the charging of the energy storage device.

11. The device of claim 10, wherein the plurality of electrodes are positioned non-transvenously.

12. The device of claim 10, wherein the means for delivering a charge from the energy storage device delivers the charge from the energy storage device if a morphology of the cardiac signal sensed by at least one of the first sensing vector and the second sensing vector during the look back sensing window is indicative of the cardiac event.

13. The device of claim 12 wherein the starting time of the predetermined look back sensing window and the ending time of the predetermined look back sensing window defines a duration between approximately 0.5 and 10 seconds.

14. The device of claim 12, wherein the means for delivering a charge from the energy storage device delivers the charge further based, at least in part, on if the cardiac signal sensed by at least one of the first sensing vector and the second sensing vector during a sensing window being different than the first predetermined look back sensing window and having a starting time and a ending time is indicative of the cardiac event, the ending time of the sensing window not being concurrent with the completion of the charging of the energy storage device.

15. The device of claim 10 wherein the starting time is based on the time of completion of the charging of the energy storage device.

16. The device of claim 10 wherein the predeteiniined look back sensing window has a fixed duration.

17. The device of claim 10 wherein the ending time of the predetermined look back sensing window is concurrent with the completion of charging.

* * * * *